US012668614B2

(12) United States Patent
Yu et al.

(10) Patent No.: US 12,668,614 B2
(45) Date of Patent: Jun. 30, 2026

(54) **USE OF *GLYCINE MAX GmSAMMT* GENE IN REGULATION OF PROTEIN CONTENT AND/OR YIELD OF PLANT**

(71) Applicant: NANJING AGRICULTURAL UNIVERSITY, Nanjing (CN)

(72) Inventors: Deyue Yu, Nanjing (CN); Guizhen Kan, Nanjing (CN); Wenjie Yuan, Nanjing (CN)

(73) Assignee: Nanjing Agricultural University, Nanjing (CN)

( * ) Notice: Subject to any disclaimer, the term of this patent is extended or adjusted under 35 U.S.C. 154(b) by 0 days.

(21) Appl. No.: 18/629,890

(22) Filed: Apr. 8, 2024

(65) Prior Publication Data

US 2024/0301013 A1     Sep. 12, 2024

Related U.S. Application Data

(63) Continuation of application No. PCT/CN2023/097288, filed on May 31, 2023.

(30) Foreign Application Priority Data

Mar. 8, 2023     (CN) .......................... 202310214014.2

(51) Int. Cl.
    *C07K 14/415*          (2006.01)
    *C12N 15/82*           (2006.01)
(52) U.S. Cl.
    CPC ........ *C07K 14/415* (2013.01); *C12N 15/8242* (2013.01); *C12N 15/8261* (2013.01)
(58) Field of Classification Search
    CPC .............. C07K 14/415; C12N 15/8242; C12N 15/8261
    See application file for complete search history.

(56) References Cited

U.S. PATENT DOCUMENTS 10,696,975 B2 *   6/2020   Coffin ................ C12N 15/8271

OTHER PUBLICATIONS

GenBank reference U43683.1: https://www.ncbi.nlm.nih.gov/nuccore/1399379 (Year: 1996).*
UniProt entry I1JN67_SOYBN: https://www.uniprot.org/uniprotkb/I1JN67/entry (Year: 2012).*
Joshi et al (1998) Plant Molecular Biology. 37: 663-674. (Year: 1998).*

(Continued)

*Primary Examiner* — Anne Kubelik
*Assistant Examiner* — Victoria L Deleo
(74) *Attorney, Agent, or Firm* — Fish IP Law, LLP

(57)          ABSTRACT

The present disclosure relates to the technical field of genetic engineering, and in particular to a use of a *Glycine max* GmSAMMT gene in regulation of a protein content and/or a yield of a plant. The present disclosure has proved through experiments that an expression level of the GmSAMMT gene in a GmSAMMT-knockout line is significantly lower than an expression level of the GmSAMMT gene in a control line, and a protein content and a seed weight of a GmSAMMT-knockout line are significantly higher than a protein content and a seed weight of a control line. Compared with the control line, in a GmSAMMT-overexpressed line, a transcription level of the GmSAMMT gene is significantly increased, a protein content is significantly reduced, and a seed weight is also reduced without a significant difference.

1 Claim, 15 Drawing Sheets

Specification includes a Sequence Listing.

(56)     References Cited

OTHER PUBLICATIONS

Feng et al (2024) Synthetic and Systems Biotechnology. 9(2): 340-348. (Year: 2024).*

Roje (2006) Phytochemistry. 67: 1686-1698. (Year: 2006).*

Guo et al (2020) Oil Crop Science. 5(1):11-16. (Year: 2020).*

Chromy et al (2015) Critical Reviews in Analytical Chemistry. 45:106-111. (Year: 2015).*

Tukuli, A. R. (2022). Increasing methionine content of soybean using CRISPR/Cas9 and developing machine learning predictive models. Doctoral dissertation, University of Missouri-Columbia. (Year: 2022).*

Teshima et al (2020) Plant Physiology. 183: 934-956. (Year: 2020).*

GenBank reference NM_ 001317717.2: https://www.ncbi.nlm.nih. gov/nuccore/NM_001317717.2 (Year: 2021).*

Adebisi et al (2017) Biochemistry and Molecular Biology. 2(2): 8-11. (Year: 2017).*

* cited by examiner 750 bp ⟶ a b b

```
                             NGG
(SEQ ID NO: 25) WT:   CCCTGCATTGGTTTGACCGCCCAA (SEQ ID NO: 27) KO_#1: CCCTGC········CCGCCCAA         -10 bp (SEQ ID NO: 29) KO_#2: CCCTGCA··GGTTTGACCGCCCAA        -2 bp

NGG
(SEQ ID NO: 26) WT:   GATCATGGTCAGCATATCAGACGG (SEQ ID NO: 28) KO_#1: GATCATGGTCAGCA····AGACGG         -4 bp (SEQ ID NO: 30) KO_#2: GATCATGGTCAGC······GACGG         -6 bp
```

FIG. 6B a b b

USE OF *GLYCINE MAX GmSAMMT* GENE IN REGULATION OF PROTEIN CONTENT AND/OR YIELD OF PLANT

CROSS REFERENCE TO RELATED APPLICATION

The present application is a national stage application of International Patent Application No. PCT/CN2023/097288, filed on May 31, 2023, which claims priority to Chinese Patent Application CN202310214014.2 filed to the China National Intellectual Property Administration (CNIPA) on Mar. 8, 2023 and entitled "USE OF *GLYCINE MAX* GmSAMMT GENE IN REGULATION OF PROTEIN CONTENT AND/OR YIELD OF PLANT", which is incorporated herein by reference in its entirety.

REFERENCE TO SEQUENCE LISTING

A computer readable XML file entitled "GWPCTP20231209965_seqlist", that was created on Mar. 6, 2024, with a file size of about 27,708 bytes, contains the sequence listing for this application, has been filed with this application, and is hereby incorporated by reference in its entirety.

TECHNICAL FIELD

The present disclosure relates to the technical field of genetic engineering, and in particular to a use of a *Glycine max* GmSAMMT gene in regulation of a protein content and/or a yield of a plant.

BACKGROUND

Proteins (known as plant proteins) extracted from crops (such as *Glycine max, Zea mays*, and *Triticum aestivum*) are often produced as by-products during production of foods such as edible oils and starches. The production of plant proteins consumes less natural resources than the production of animal-derived proteins, and thus is considered to be more beneficial to the environment than the production of animal-derived proteins. *Glycine max* (L.) Merr. is a main source of plant proteins, and plays an irreplaceable role in the daily life. Seeds of *Glycine max* are rich in proteins, and have a protein content of 35% to 42%. A protein content and a yield of seeds of *Glycine max* are important traits of *Glycine max*, and thus the elucidation of genetic and molecular mechanisms of these two traits is of great significance for improvement of a yield and quality of seeds of *Glycine max*.

S-adenosyl-L-methionine methyltransferase has been widely studied in animals and *Escherichia coli*, but the research on S-adenosyl-L-methionine methyltransferase in plants has rarely been reported. Studies in *Arabidopsis thaliana* have shown that methionine is an essential metabolite in plant cells, and S-adenosylmethionine (SAM) is a first metabolite of methionine and can regulate the levels of various metabolites such as ethylene, polyamines, and biotin. SAM is a major biological methyl donor in organisms, and a methyl donation process of SAM is catalyzed by S-adenosyl-L-methionine methyltransferase. A function of a gene of such an enzyme in *Glycine max* has not been reported.

SUMMARY

In order to solve the above problems, the present disclosure provides a use of a *Glycine max* GmSAMMT gene in regulation of a protein content and/or a yield of a plant. The *Glycine max* GmSAMMT gene of the present disclosure can regulate a protein content and/or a yield of a plant, and the knockout of the GmSAMMT gene can significantly increase a protein content of soybeans and can also significantly increase a seed weight.

To allow the above objective, the present disclosure provides the following technical solutions:

The present disclosure provides a use of a *Glycine max* GmSAMMT gene in one or more selected from the group consisting of the following aspects:

1) regulation of a protein content of a plant; 2) regulation of a seed weight of a plant; 3) regulation of a seed length of a plant; 4) regulation of a seed width of a plant; and 5) regulation of a seed thickness of a plant, where a protein encoded by the GmSAMMT gene has an amino acid sequence shown in SEQ ID NO: 1.

Preferably, the regulation of a protein content of a plant includes: negatively regulating an expression level of the GmSAMMT gene to increase the protein content of the plant, or positively regulating an expression level of the GmSAMMT gene to reduce the protein content of the plant.

Preferably, the protein includes a protein in a plant seed.

Preferably, the regulation of a seed weight of a plant includes negatively regulating an expression level of the GmSAMMT gene to increase the seed weight of the plant;

the regulation of a seed length of a plant includes negatively regulating an expression level of the GmSAMMT gene to increase the seed length of the plant;

the regulation of a seed width of a plant includes negatively regulating an expression level of the GmSAMMT gene to increase the seed width of the plant; and the regulation of a seed thickness of a plant includes negatively regulating an expression level of the GmSAMMT gene to increase the seed thickness of the plant.

Preferably, the plant includes a leguminous plant.

Preferably, the leguminous plant includes *Glycine max*.

The present disclosure also provides a use of a *Glycine max* GmSAMMT gene in breeding of a high-protein and/or high-yield transgenic plant, where a protein encoded by the GmSAMMT gene has an amino acid sequence shown in SEQ ID NO: 1.

Preferably, the plant includes a leguminous plant.

Preferably, the leguminous plant includes *Glycine max*.

The present disclosure also provides a sgRNA for knockout of a GmSAMMT gene, including amplification primers for knockout of a target, where the amplification primers have nucleotide sequences shown in SEQ ID NO: 11-18, respectively.

The present disclosure also provides a recombinant vector for knockout of a GmSAMMT gene, where the recombinant vector is constructed by a method including the following steps:

with a pGmU3 plasmid as a template, conducting polymerase chain reaction (PCR) amplification using amplification primers shown in SEQ ID NO: 11 and SEQ ID NO: 12 to obtain a first amplification product;

with a pGmU3 plasmid as a template, conducting PCR amplification using amplification primers shown in SEQ ID NO: 13 and SEQ ID NO: 14 to obtain a second amplification product;

with a pGmU6 plasmid as a template, conducting PCR amplification using amplification primers shown in SEQ ID NO: 15 and SEQ ID NO: 16 to obtain a third amplification product;

with a pGmU6 plasmid as a template, conducting PCR amplification using amplification primers shown in SEQ ID NO: 17 and SEQ ID NO: 18 to obtain a fourth amplification product;

subjecting the first amplification product and the second amplification product to bridging PCR to obtain a reaction product A, and subjecting the third amplification product and the fourth amplification product to bridging PCR to obtain a reaction product B;

with the reaction product A as a template, conducting PCR amplification using amplification primers shown in SEQ ID NO: 11 and SEQ ID NO: 14 to obtain an amplification product U3-sgRNA1;

with the reaction product B as a template, conducting PCR amplification using amplification primers shown in SEQ ID NO: 15 and SEQ ID NO: 18 to obtain an amplification product U6-sgRNA2;

subjecting the amplification product U3-sgRNA1, the amplification product U6-sgRNA2, and a pSC-M vector to enzyme cleavage, separately; and subjecting enzyme cleavage products of the amplification product U3-sgRNA1, the amplification product U6-sgRNA2, and the pSC-M vector as templates to a ligation reaction with a T4 ligase to obtain the recombinant vector.

Beneficial Effects

The present disclosure provides a use of a *Glycine max* GmSAMMT gene in one or more selected from the group consisting of the following aspects: 1) regulation of a protein content of a plant; 2) regulation of a seed weight of a plant; 3) regulation of a seed length of a plant; 4) regulation of a seed width of a plant; and 5) regulation of a seed thickness of a plant, where a protein encoded by the GmSAMMT gene has an amino acid sequence shown in SEQ ID NO: 1. In the present disclosure, a CRISPR-Cas9 technology is used for site-directed editing of the *Glycine max* GmSAMMT gene to obtain two lines in which the GmSAMMT gene is edited. Quantitative reverse transcription polymerase chain reaction (qRT-PCR) results show that an expression level of the GmSAMMT gene in a GmSAMMT-knockout line is significantly lower than an expression level of the GmSAMMT gene in a control line, and a protein content and a seed weight of a GmSAMMT-knockout line are significantly higher than a protein content and a seed weight of a control line. Compared with the control line, in a GmSAMMT-overexpressed line, a transcription level of the GmSAMMT gene is significantly increased, a protein content is significantly reduced, and a seed weight is also reduced without a significant difference. Subcellular localization results show that GmSAMMT is localized in a cell nucleus. Results of seed weight and protein content changes in a GmSAMMT-knockout transgenic *Glycine max* material show that the GmSAMMT gene can negatively regulate a seed weight and a protein content of *Glycine max*, and the knockout of the GmSAMMT gene can improve the yield and quality traits of *Glycine max*.

Therefore, the GmSAMMT gene can be used in improvement of a nutritional quality of *Glycine max*.

BRIEF DESCRIPTION OF THE DRAWINGS

To explain the technical solutions in the embodiments of the present disclosure or in the prior art clearly, the accompanying drawings required in the embodiments will be briefly described below.

FIGS. 6A-6B show schematic diagram of acquisition of a GmSAMMT-knockout transgenic material and sequencing results of the GmSAMMT-knockout transgenic material;

DETAILED DESCRIPTION OF THE EMBODIMENTS

Figure 1:
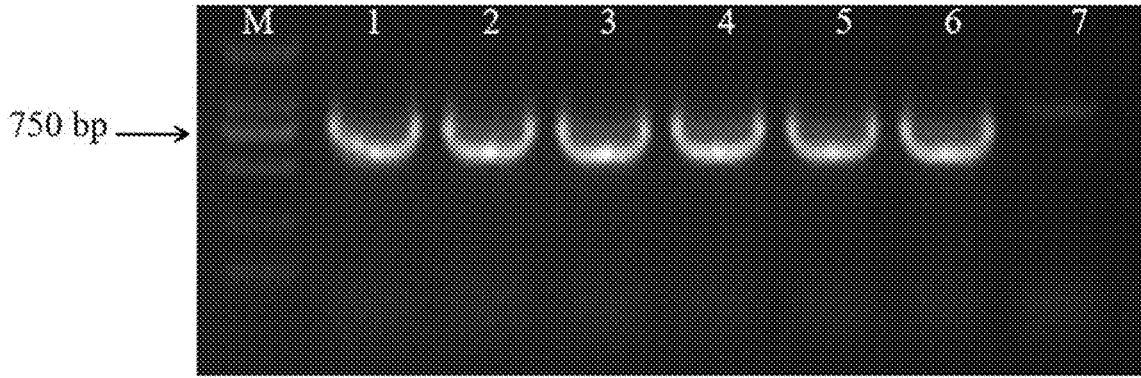
FIG. 1 shows PCR amplification results of GmSAMMT.

The present disclosure provides a use of a *Glycine max* GmSAMMT gene in one or more selected from the group consisting of the following aspects:

1) regulation of a protein content of a plant; 2) regulation of a seed weight of a plant; 3) regulation of a seed length of a plant; 4) regulation of a seed width of a plant; and 5) regulation of a seed thickness of a plant, where a protein (which is denoted as a GmSAMMT protein) encoded by the GmSAMMT gene has an amino acid sequence shown in SEQ ID NO: 1, which is specifically as follows:

```
MAKLFLKQAKQYADARPSYPPQLFQFIASKTPSHNLAWDVGTGSGQA

AKSLAAIYKNVIATDASDKQLEFAAKLPNVRYQHTPSTMSTAELEQM

VASKGTIDLVTIAQALHWFDRPTFYEQVKWVLKKPHGIIAAWCYYLP

RVSDAFDTVFDQFYSTNVSPYWDPARKWVDDNYRSIDFPFEPVDGAD

HTGPFEFVTETMMDLDDFLTYIRSWSAYQTAKEKGVELLAEDVVEKF

KLAWGEDAKKVVKFPIYLRIGRTGDS.
```

In the present disclosure, the GmSAMMT gene has a nucleotide sequence preferably shown in SEQ ID NO: 2, which is specifically as follows:

```
5'-ttcaggacgcaacgggggtgatggcatcatggttattacagaat aaatgattgaagagtgatggaaggttcttgcttttgtttgtatatat acatactattattgctaggaaattgaagacctaagatacaatagaga tggcaaagctatttttgaaacaggcaaagcaatacgcagatgcaaga ccaagctatcctccacaactcttccaattcattgcttccaagactcc
```

5

-continued

```
ctctcacaacctcgcttgggacgtcggcactgggagcggccaagctg ccaaatctttagctgcaatatacaagaatgtgatagccacagatgct agtgacaaacaacttgaatttgcagccaagctcccaaatgtgagata ccaacacacccttcaaccatgtcgacggccgagcttgaacaaatgg tggcatctaagggaaccatagaccttgtgaccatagcacaagccctg cattggtttgaccgcccaaccttctacgaacaagtgaagtgggttct caagaaacctcatggaatcattgctgcttggtgttactatttgccaa gagttagtgatgcatttgacactgtctttgaccaattctattccact aatgtaagcccttattgggacccagctcgtaaatgggttgatgacaa ttatagaagcattgattttccatttgagcccgtggatggagctgatc acacaggacccttgagtttgtgacggaaacaatgatggatttggat gatttcttgacctacataagatcatggtcagcatatcagacggctaa ggagaaaggagtggagcttctcgcggaggatgtggttgaaaaattca agcttgcttggggtgaagatgctaaaaaagttgtcaagtttccaatt tatttgagaattggaagaacaggggattcctaaagacatatgcaaat ggttgcttttactgtgtgggagatgtgacgagtaccaacttttatga gtttatccattgattgaataatgtaattttattgaattgcgttcatg ttaagtcaaaagctttaaattcgaagggtacaattcctacttatct ggaaagagttgagccttagtttgctatgttaattttgtaatttggta ttgataaattttgttgtgtgtgtcaaccaaattttgatagaaaagta cttgtagtaaatacttgataatttattttaatgatgttaaattaagg tatttgc-3',
``` where an underscored sequence is a coding sequence (CDS).

In the present disclosure, the regulation of a protein content of a plant preferably includes: negatively regulating an expression level of the GmSAMMT gene to increase the protein content of the plant, or positively regulating an expression level of the GmSAMMT gene to reduce the protein content of the plant. The protein preferably includes a protein in a plant seed.

In the present disclosure, the regulation of a seed weight of a plant preferably includes negatively regulating an expression level of the GmSAMMT gene to increase the seed weight of the plant;

the regulation of a seed length of a plant preferably includes negatively regulating an expression level of the GmSAMMT gene to increase the seed length of the plant;

the regulation of a seed width of a plant preferably includes negatively regulating an expression level of the GmSAMMT gene to increase the seed width of the plant; and the regulation of a seed thickness of a plant preferably includes negatively regulating an expression level of the GmSAMMT gene to increase the seed thickness of the plant.

In the present disclosure, the plant preferably includes a leguminous plant, and the leguminous plant preferably includes Glycine max.

In the present disclosure, with Jack as an acceptor material, a GmSAMMT gene-overexpression vector and a CRISPR/Cas9 vector each are constructed and transformed into Glycine max to obtain a GmSAMMT gene-overexpressed $T_0$-generation Glycine max plant and a GmSAMMT gene-knockout $T_0$-generation Glycine max plant. qRT-PCR results show that an expression level of the GmSAMMT gene in a GmSAMMT-knockout line is significantly lower than an expression level of the GmSAMMT gene in a control line, and a protein content and a seed weight of a GmSAMMT-knockout line are significantly higher than a protein content and a seed weight of a control line. Compared with the control line, in a GmSAMMT-overexpressed line, a transcription level of the GmSAMMT gene is significantly increased, a protein content is significantly reduced, and a seed weight is also reduced without a significant difference. Subcellular localization results show that GmSAMMT is localized in a cell nucleus. Results of seed weight and protein content changes in a GmSAMMT-knockout transgenic Glycine max material show that the GmSAMMT gene can negatively regulate a seed weight and a protein content of Glycine max, and the knockout of the GmSAMMT gene can improve the yield and quality traits of Glycine max. Therefore, the GmSAMMT gene can be used in improvement of a nutritional quality of Glycine max.

The present disclosure also provides a use of a Glycine max GmSAMMT gene in breeding of a high-protein and/or high-yield transgenic plant.

In the present disclosure, the plant preferably includes a leguminous plant, and the leguminous plant preferably includes Glycine max.

In the present disclosure, the use preferably includes knocking out the Glycine max GmSAMMT gene or interfering with an expression level of the Glycine max GmSAMMT gene by means of gene editing.

The present disclosure also provides a sgRNA for knockout of a GmSAMMT gene, including amplification primers for knockout of a target, where the amplification primers have nucleotide sequences shown in SEQ ID NO: 11-18, respectively.

The sgRNA provided by the present disclosure simultaneously targets two exon regions of the GmSAMMT gene, such that the GmSAMMT gene can be effectively knocked out and an expression level of the GmSAMMT gene can be reduced.

The present disclosure also provides a recombinant vector for knockout of a GmSAMMT gene, where the recombinant vector is constructed by a method including the following steps:

with a pGmU3 plasmid as a template, PCR amplification is conducted using amplification primers shown in SEQ ID NO: 11 and SEQ ID NO: 12 to obtain a first amplification product;

with a pGmU3 plasmid as a template, PCR amplification is conducted using amplification primers shown in SEQ ID NO: 13 and SEQ ID NO: 14 to obtain a second amplification product;

with a pGmU6 plasmid as a template, PCR amplification is conducted using amplification primers shown in SEQ ID NO: 15 and SEQ ID NO: 16 to obtain a third amplification product;

with a pGmU6 plasmid as a template, PCR amplification is conducted using amplification primers shown in SEQ ID NO: 17 and SEQ ID NO: 18 to obtain a fourth amplification product;

the first amplification product and the second amplification product are subjected to bridging PCR to obtain a reaction product A, and the third amplification product and the fourth amplification product are subjected to bridging PCR to obtain a reaction product B;

with the reaction product A as a template, PCR amplification is conducted using amplification primers shown in SEQ ID NO: 11 and SEQ ID NO: 14 to obtain an amplification product U3-sgRNA1;

with the reaction product B as a template, PCR amplification is conducted using amplification primers shown in SEQ ID NO: 15 and SEQ ID NO: 18 to obtain an amplification product U6-sgRNA2;

the amplification product U3-sgRNA1, the amplification product U6-sgRNA2, and a pSC-M vector are subjected to enzyme cleavage, separately; and enzyme cleavage products of the amplification product U3-sgRNA1, the amplification product U6-sgRNA2, and the pSC-M vector as templates are subjected to a ligation reaction with a T4 ligase to obtain the recombinant vector.

In the present disclosure, the pGmU3 (reverse) is a U3-sgRNA1 backbone preservation vector, the pGmU6 (forward) is a U6-sgRNA2 backbone preservation vector, and the pSC-M (S represents sgRNA, C represents Cas9, and M represents multiply-target) is a CRISPR/Cas9 multi-knock-out vector; and these vectors are modified in the laboratory of the present disclosure, as shown in the literature (Du, H., Zeng, X., Zhao, M., Cui, X., Wang, Q., Yang, H., Cheng, H., & Yu, D. (2016). Efficient targeted mutagenesis in soybean by TALENs and CRISPR/Cas9. Journal of biotechnology, 217, 90-97. https://doi.org/10.1016/j.jbiotec.2015.11.005).

In order to further illustrate the present disclosure, the use of a *Glycine max* GmSAMMT gene in regulation of a protein content and/or a yield of a plant provided in the present disclosure is described in detail below with reference to the accompanying drawings and examples, but the accompanying drawings and examples should not be understood as limiting the protection scope of the present disclosure.

Example 1

1) Cloning of a GmSAMMT Gene Encoding S-Adenosyl-L-Methionine Methyltransferase in *Glycine max*

A corresponding GmSAMMT gene (Glyma.03G129300, Gene ID: 100784891) was found from the National Center for Biotechnology Information (NCBI) database and the Phytozome v12 *Glycine max* database, and specific primers were designed according to a nucleotide sequence provided by the databases and used to amplify CDS of the GmSAMMT gene. Sequences of the specific primers were shown in SEQ ID NO: 3 (5'-GGATCTTCCAGAGATGTAGT-CATGGTAGTCTGCACCA-3') and SEQ ID NO: 4 (5'-CTGCCGTTCGACGATACTCGTCACATCTCCCACAC-3'), respectively. Leaves were collected from a *Glycine max* variety Jack, ground with liquid nitrogen, and placed in a 1.5 mL EP tube, then 1 mL of a lysis buffer was added, the EP tube was vortexed to allow thorough mixing, and extraction was then conducted according to a kit (Total RNA Kit, Tiangen, Beijing, China). A mass of total RNA was identified by formaldehyde denaturing gel electrophoresis, and an RNA content was determined by spectrophotometer. The total RNA obtained above as a template was reverse-transcribed according to instructions of a reverse transcription kit (Vazyme® HiScript 1st Strand cDNA Synthesis Kit, Nanjing) provided by Vazyme® to obtain a first strand of cDNA, and then PCR amplification was conducted. A 50 μL PCR system included the following components: 2 μL of the template, 2 μL of each of upstream and downstream primers, 1 μL of dNTP Mix, 25 μL of 2×Phanta® Max Buffer, 1 μL of Phanta® Max Super-Fidelity DNA Polymerase, and the balance of ddH$_2$O. A PCR procedure was as follows: pre-denaturation at 95° C. for 3 min; denaturation at 95° C. for 15 s, annealing at 58° C. for 15 s, and extension at 72° C. for 60 s, with 35 cycles in total; and finally, thorough extension at 72° C. for 5 min, and heat preservation at 4° C. for 0.5 h.

PCR amplification results are shown in FIG. 1 with lanes M, 1, 2, 3, 4, 5, 6, and 7 from left to right, where M represents a marker (DL2000); the brightest band is 750 bp; lanes 1 to 6 represent target bands of GmSAMMT; and a lane 7 represents a negative control. A gel was recovered and subjected to PCR product purification, ligation, and transformation, and positive monoclones were picked for sequencing to obtain CDS of the *Glycine max* GmSAMMMT gene that included a complete coding region and had a length of 786 bp (the underscored sequence shown in SEQ ID NO: 2).

2) Analysis of Expression of the GmSAMMT Gene in Tissues

In order to identify expression levels of GmSAMMT in different tissues, roots, stems, leaves, flowers, pods, and seeds were collected from a Jack variety at different development stages, where the roots, stems, and leaves were collected at a V4 stage; the flowers were collected at an R2 stage; the seeds were collected on day 15 (15 DAF seed) and day 45 (45 DAF seed); and the pods were collected on day 15 (15 DAF pod) and day 45 (45 DAF pod) after flowering. 3 parallel replicates were set for each material. Each sample was quickly frozen with liquid nitrogen and then stored at −80° C. The extraction of total RNA was the same as in step 1). Total RNA extracted from each of the above tissues as a template was reverse-transcribed into cDNA according to instructions of a HiScript III 1st Strand cDNA Synthesis Kit (+gDNA wiper (Vazyme®, China)). qRT-PCR detection was conducted according to instructions of a ChamQTMSYBR®qPCR Master Mix kit (Vozyme, China). A 20.0 μL qRT-PCR system was as follows: 10 μL of 2×ChamQ SYBRqPCR Master Mix, 0.4 μL of Primer 1 (10 μM), 0.4 μL of Primer 2 (10 μM), 0.4 μL of 50×ROX Reference Dye 1, 5 μL of Template DNA/cDNA, and the balance of ddH$_2$O. A qRT-PCR reaction procedure was as follows: pre-denaturation at 95° C. for 30 s; and denaturation at 95° C. for 10 s and extension at 60° C. for 30 s, with 40 cycles in total. A dissolution curve involved dissolution at 95° C. for 15 s, dissolution at 60° C. for 1 min, and dissolution at 95° C. for 15 s. Primer sequences for fluorescence quantification of GmSAMMT were shown in SEQ ID NO: 5 (5'-GAATTTGCAGCCAAGCTCCC-3') and SEQ ID NO: 6 (5'-CAGGGCTTGTGCTATGGTCA-3'), respectively.

Figure 2:
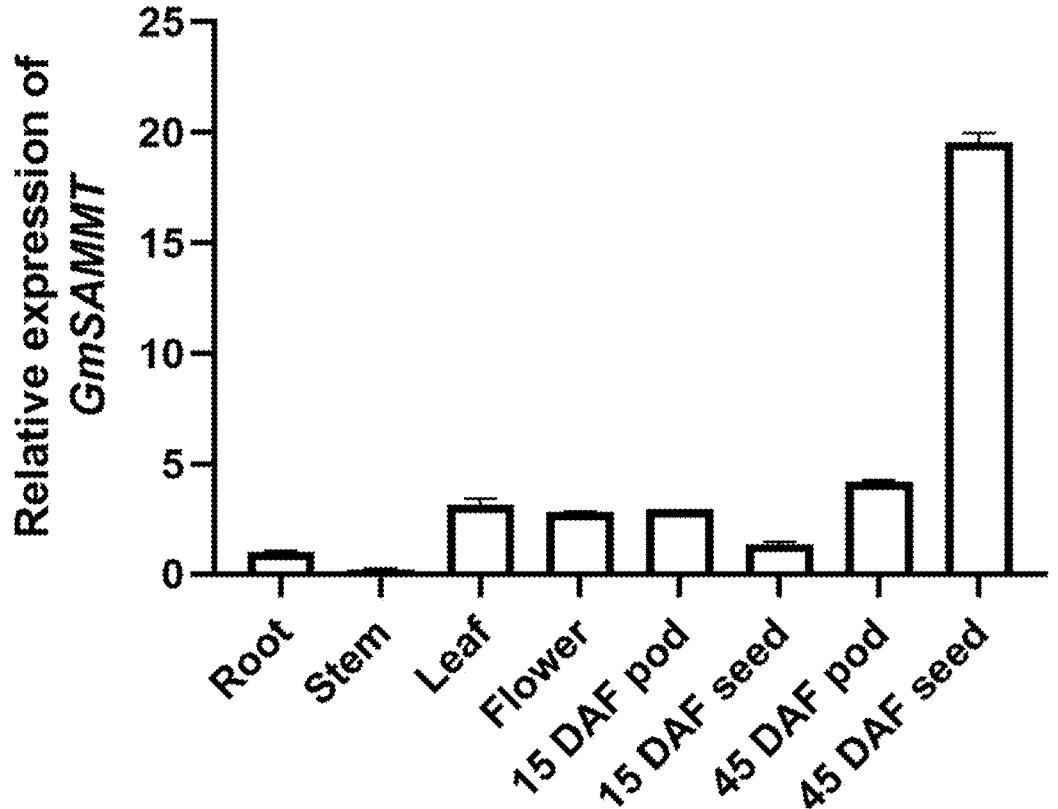
FIG. 2 shows analysis results of expression levels of GmSAMMT in tissues.

Analysis results of expression levels of GmSAMMT in the tissues are shown in FIG. 2. The analysis results show that GmSAMMT is a constitutively-expressed gene, can be expressed in various tissues of *Glycine max*, and has a maximum expression level in the 45 DAF seeds and a minimum expression level in the roots, stems, and 15 DAF seeds.

3) Subcellular Localization of the GmSAMMT Gene

Figure 3A:
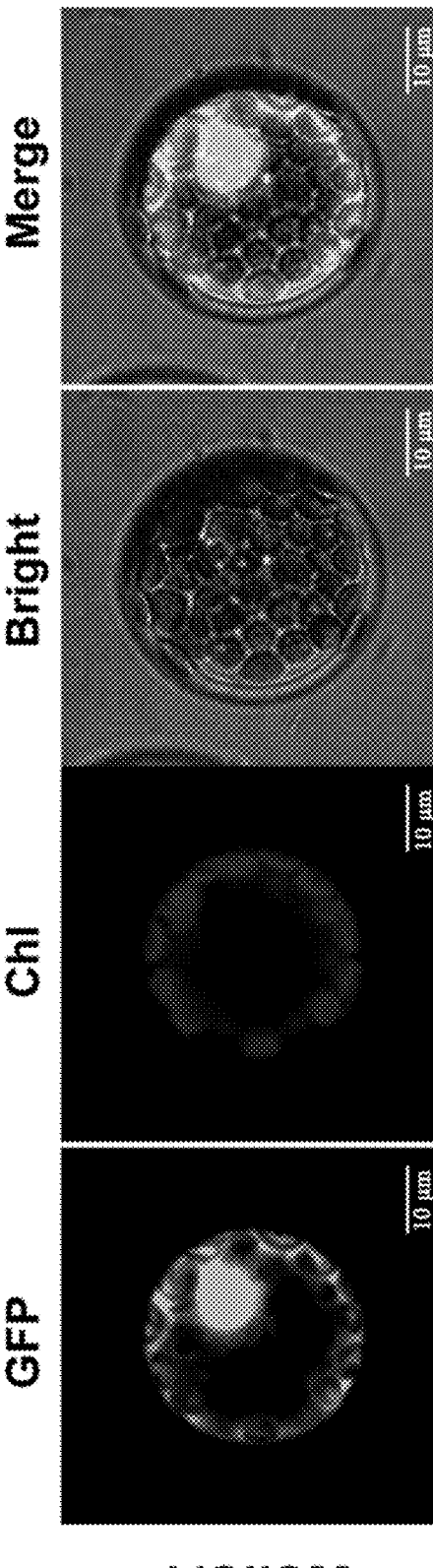
FIGS. 3A-3B show subcellular localization results of a GmSAMMT gene.
Figure 3B:
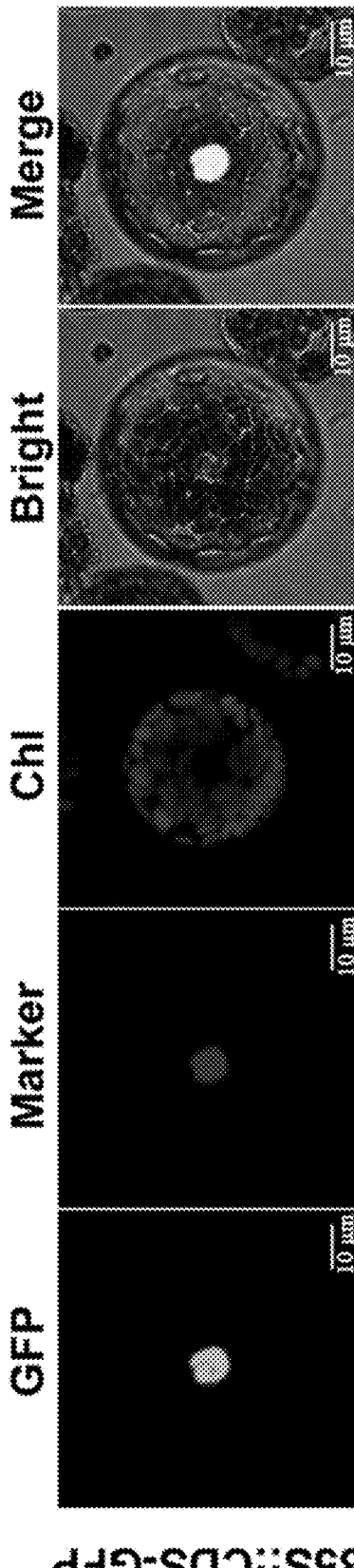

Primers including intact CDS of the GmSAMMT gene (without a stop codon) were designed, and sequences of the primers were shown in SEQ ID NO: 7 (5'-TACAAATC-TATCTCTCTCGAGATGGCAAAGCTATTTTTGAA-3') and SEQ ID NO: 8 (5'-TGCTCACCATG-GATCCCCGGGGGAATCCCCTGTTCTTCCAA-3'), respectively. A specific PCR process was the same as in step 1). PCR amplification was conducted with a high-fidelity polymerase of Vazyme® (Phanta® Max Super-Fidelity DNA Polymerase), an amplification product was recovered with a gel, and a recovered product and a vector each were subjected to double enzyme cleavage with restriction endonucleases SmaI and XhoI overnight at 37° C. A 10.0 μL enzyme cleavage system included the following components: 1 μL of each of restriction endonucleases SmaI and XhoI, 100 μg of a template, and the balance of ddH$_2$O. Enzyme cleavage products were subjected to ligation with a T4 DNA ligase in a PCR instrument at 22° C. for 1 h. A 20 μL ligation system included the following components: 4 μL of a vector fragment, 8 μL of a target gene fragment, 2 μL of 10×T$_4$ DNAligase Buffer, 1 μL of T$_4$ DNA ligase (400 u/μL), and the balance of ddH$_2$O. Then, a ligation product was transformed into bacteria, transformed bacteria were plated, and a plasmid was extracted from bacteria with a correct sequence and named pAN58-GmSAMMT. The plasmid and an empty plasmid each were transformed into an EHA105 competent cell by a freeze-thaw method, and then transiently transformed into an *Arabidopsis thaliana* protoplast by a polyethylene glycol (PEG) method. A transformed protoplast was cultivated for 48 h at 28° C. in the dark, and then the luminescence of the protoplast was observed under a laser scanning confocal microscope (LSCM) (ZEISS, LSM780). Results are shown in FIGS. 3A-3B, where results of transformation of the empty plasmid are shown in the first row, including a fluorescence channel, a chloroplast fluorescence channel, a bright field, and an overlay image from left to right; and results of transformation of the pAN58-GmSAMMT vector are shown in the second row, including a target protein fluorescence channel, a Marker fluorescence channel, a chloroplast fluorescence channel, a bright field, and an overlay image from left to right. The results show that the GmSAMMT protein is localized on a cell nucleus.

Example 2 Genetic Engineering Application of the GmSAMMT Gene

1) Cloning of an Enzyme Cleavage Site-Containing Sequence in a GmSAMMT Gene Encoding S-Adenosyl-L-Methionine Methyltransferase in *Glycine max*

Total RNA of seeds of a *Glycine max* variety Jack as a template was reverse-transcribed to obtain a first strand of cDNA, and then PCR amplification was conducted with primer sequences shown in SEQ ID NO: 9 (5'-GGGCCCAGGCCTACGCGTATGGCAAAGCTATTTTT-GAA-3') and SEQ ID NO: 10 (5'-TCGGGGAAAT-TCGAGCTCTTAGGAATCCCCTGTTCTTC-3'), respectively. A 50 μL amplification system included the following components: 2 μL of a template, 2 μL of each of upstream and downstream primers, 1 μL of dNTP Mix, 25 μL of 2×Phanta® Max Buffer, 1 μL of Phanta® Max Super-Fidelity DNA Polymerase, and the balance of ddH$_2$O. A PCR procedure was as follows: pre-denaturation at 95° C. for 3 min; denaturation at 95° C. for 15 s, annealing at 58° C. for 15 s, and extension at 72° C. for 60 s, with 35 cycles in total; and finally, thorough extension at 72° C. for 5 min, and heat preservation at 4° C. After sequencing, CDS of the *Glycine max* GmSAMMT gene that included a complete coding region and had a length of 786 bp (the underscored sequence shown in SEQ ID NO: 2) was obtained.

2) Construction of a Plant Overexpression Vector

Figure 4:
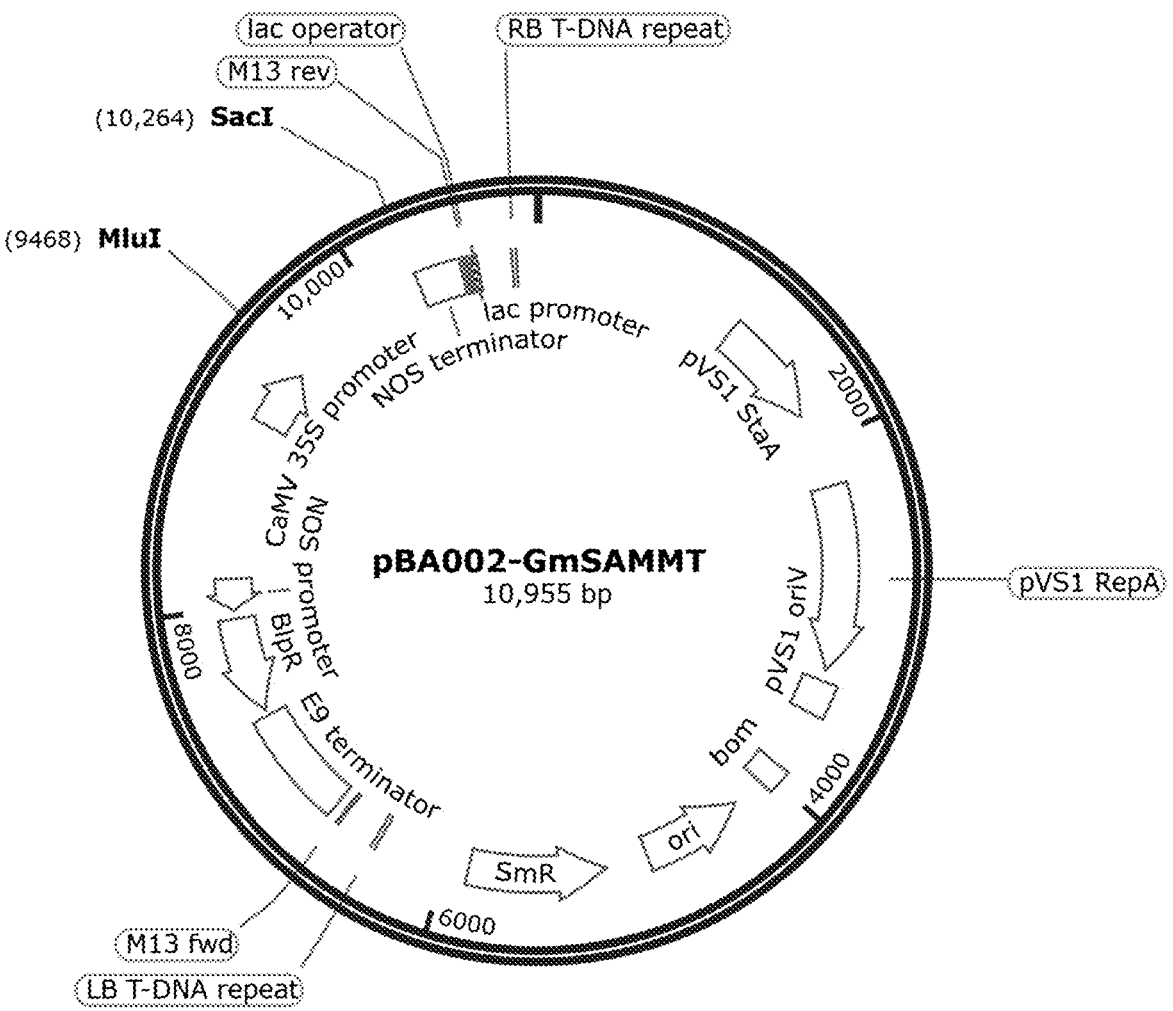
FIG. 4 is a schematic diagram of a GmSAMMT-overexpression vector.

The overexpression vector was constructed by a homologous recombination method. A target gene fragment with an enzyme cleavage linker amplified using the primers shown in SEQ ID NO: 9 and SEQ ID NO: 10 in step 1) and the pBA002 vector were subjected to a recombination reaction with a ClonExpress® Entry One Step Cloning Kit (C115) of Vazyme®. A 10 μL recombination reaction system included the following components: 1 μL of a vector, 2 μL of a target fragment, 5 μL of 2×CloneExpressMix, and the balance of ddH$_2$O. The recombination reaction was conducted at 50° C. for 5 min. A recombinant product was transformed into bacteria, transformed bacteria were plated, and monoclones were picked and verified by bacterial-liquid PCR sequencing. Primers for the sequencing were shown in SEQ ID NO: 21 (5'-ATGACGCACAATCCCA-3') and SEQ ID NO: 10, respectively. Finally, the plant overexpression plasmid pBA002-GmSAMMT was obtained and stored in a refrigerator at −20° C. for later use. A schematic diagram of the GmSAMMT-overexpression vector is shown in FIG. 4, and a sequence between restriction endonucleases Miu I and Sac I is CDS of the target gene GmSAMM.

3) Construction of a Plant Knockout Vector

A *Glycine max* GmSAMMT gene sequence was downloaded from the phytozome (https://phytozome.jgi.doe-.gov/). A sgRNA target sequence included amplification primers for targets: SEQ ID NO: 11 (5'-CATGC-CATGGTAGAGGAGCTGTTCTGCTTC-3') and SEQ ID NO: 12 (5'-TCTGATATGCTGACCATGATTGACCAGA-CATGTCACGCTT-3'), SEQ ID NO: 13 (5'-AT-CATGGTCAGCATATCAGAGTTT-TAGAGCTAGAAATAGC-3') and SEQ ID NO: 14 (5'-GTCAGTCGAC CATGAATAGGTCTATGACC-3'), SEQ ID NO: 15 (5'-GTCAGTCGACGGAATTGTGAGCGGA-TAAC-3') and SEQ ID NO: 16 (5'-TGCAT-TGGTTTGACCGCCCAAATCCATATGTTTTCCTGGG-3'), and SEQ ID NO: 17 (5'-TGGGCGGTCAAACCAATGCAGTTTTAGAGCTAGAA ATAGC-3') and SEQ ID NO: 18 (5'-CTAGTCTAGACCAT-GAATAGGTCTATGACC-3').

With a pGmU3 plasmid as a template, PCR amplification was conducted using amplification primers shown in SEQ ID NO: 11 and SEQ ID NO: 12 to obtain a first amplification product;

with a pGmU3 plasmid as a template, PCR amplification was conducted using amplification primers shown in SEQ ID NO: 13 and SEQ ID NO: 14 to obtain a second amplification product;

with a pGmU6 plasmid as a template, PCR amplification was conducted using amplification primers shown in SEQ ID NO: 15 and SEQ ID NO: 16 to obtain a third amplification product; and with a pGmU6 plasmid as a template, PCR amplification was conducted using amplification primers shown in SEQ ID NO: 17 and SEQ ID NO: 18 to obtain a fourth amplification product.

A 50 μL PCR system for each of the first, second, third, and fourth amplification products included the following components: 25 μL of 2×Phanta® Max Buffer, 1 μL of Phanta® Max Super-Fidelity DNA Polymerase, 1 μL of dNTP, 1 μL of a pGmU3/pGmU6 plasmid, 1 μL of each of left and right primers, and the balance of ddH$_2$O.

A PCR procedure for each of the first, second, third, and fourth amplification products was as follows: pre-denaturation at 95° C. for 5 min; denaturation at 95° C. for 15 s, annealing at 57° C. for 20 s, and extension at 72° C. for 18 s, with 35 cycles in total; and thorough extension at 72° C. for 5 min.

The first amplification product and the second amplification product were subjected to bridging PCR to obtain a reaction product A, and the third amplification product and the fourth amplification product were subjected to bridging PCR to obtain a reaction product B. A 50 μL bridging PCR system included the following components: 500 ng of the first or third amplification product, 300 ng of the second or fourth amplification product, 1 μL of dNTP Mix, 25 μL of 2×Phanta® Max Buffer, 1 μL of Phanta® Max Super-Fidelity DNA Polymerase, and the balance of ddH$_2$O. A bridging PCR procedure was as follows: pre-denaturation at 95° C. for 5 min; denaturation at 95° C. for 15 s, annealing at 57° C. for 20 s, and extension at 72° C. for 21 s, with 15 cycles in total; and thorough extension at 72° C. for 5 min.

With the reaction product A as a template, PCR amplification was conducted using amplification primers shown in SEQ ID NO: 11 and SEQ ID NO: 14 to obtain an amplification product U3-sgRNA1.

With the reaction product B as a template, PCR amplification was conducted using amplification primers shown in SEQ ID NO: 15 and SEQ ID NO: 18 to obtain an amplification product U6-sgRNA2.

A 50 μL PCR system for each of the amplification products U3-sgRNA1 and U6-sgRNA2 included the following components: 10 μL of the reaction product A or B, 1 μL of dNTP Mix, 25 μL of 2×Phanta® Max Buffer, 1 μL of Phanta® Max Super-Fidelity DNA Polymerase, 2 μL of each of left and right primers, and the balance of ddH$_2$O. A PCR procedure was as follows: pre-denaturation at 95° C. for 5 min; denaturation at 95° C. for 15 s, annealing at 57° C. for 20 s, and extension at 72° C. for 21 s, with 36 cycles in total; and thorough extension at 72° C. for 5 min.

The amplification products U3-sgRNA1 and U6-sgRNA2 and the pSC-M vector each were subjected to enzyme cleavage. A 50 μL enzyme cleavage system for the U3-sgRNA1 and U6-sgRNA2 included the following components: 5 μL of Buffer, 15 μL of U3-sgRNA1/U6-sgRNA2, 2.5 μL of NcoI, 2.5 μL of SalI, and the balance of ddH$_2$O. A 50 μL enzyme cleavage system for the pSC-M vector included the following components: 5 μL of Buffer, 6 μL of pSC-M, 2.5 μL of NcoI, 2.5 μL of SalI, and the balance of ddH$_2$O. The enzyme cleavage was conducted at 37° C. for 45 min.

Enzyme cleavage products as templates were subjected to a ligation reaction with a T$_4$ ligase. A 20 μL ligation system included the following components: 2 μL of Buffer, 150 ng of an enzyme cleavage product of the pSC-M plasmid, 60 ng of an enzyme cleavage product of U3-sgRNA1, 60 ng of an enzyme cleavage product of U6-sgRNA2, 2 μL of the T$_4$ ligase, and the balance of ddH$_2$O. The ligation reaction was conducted at 22° C. for 2 h. A ligation product was transformed into Escherichia coli TOP10, transformed Escherichia coli was cultivated overnight, and then monoclones were picked for detection. A positive bacterial solution was selected for sequencing. Primers for the sequencing were shown in SEQ ID NO: 19 (5'-AGCATTGTCTCTGCCTCT-TAAC-3') and SEQ ID NO: 20 (5'-CGTCACATCTCC-CACACAGTA-3'), respectively. A plasmid was extracted from bacteria with a correct sequence using a plasmid extraction kit and stored. Thus, a GmSAMMT gene-knock-out vector was successfully constructed.

The pGmU3 (reverse) was a U3-sgRNA1 backbone preservation vector, the pGmU6 (forward) was a U6-sgRNA2 backbone preservation vector, and the pSC-M (S represents sgRNA, C represents Cas9, and M represents multiply-target) was a CRISPR/Cas9 multi-knockout vector; and these vectors were modified in the laboratory of the present disclosure, as shown in the literature (Du, H., Zeng, X., Zhao, M., Cui, X., Wang, Q., Yang, H., Cheng, H., & Yu, D. (2016). Efficient targeted mutagenesis in soybean by TAL-ENs and CRISPR/Cas9. Journal of biotechnology, 217, 90-97. https://doi.org/10.1016/j.jbiotec.2015.11.005).

4) *Agrobacterium*-Mediated Transformation of *Glycine max* Cotyledonary Nodes

The plasmids obtained in steps 2) and 3) each were transformed into *Agrobacterium* EHA105 by a freeze-thaw method to obtain bacterial solutions pBA002-GmSAMMT and pSC-M-GmSAMMT, respectively, and a specific experimental operation process was as follows:

1. Bacterial solution preparation: The bacterial solutions pBA002-GmSAMMT and pSC-M-GmSAMMT each were streaked on an YEB plate (1 L formula: 0.5 g of peptone, 0.5 g of yeast extract, 0.5 g of sucrose, 0.05 g of MgSO$_4$·7H$_2$O, 1.5 g of agar powder, and 100 mL of pure water were mixed and then sterilized at 121° C. for 20 min) with spectinomy-cin (50 μg/mL) and kanamycin (50 μg/mL), and the YEB plate was invertedly incubated in a shaker at 28° C. until monoclones grew. Monoclones were picked and inoculated into an YEB liquid medium (1 L formula: 0.5 g of peptone, 0.5 g of yeast extract, 0.5 g of sucrose, 0.05 g of MgSO$_4$·7H$_2$O, and 100 mL of pure water were mixed and then sterilized at 121° C. for 20 min) with a corresponding antibiotic, cultivated overnight in a shaker at 28° C., then transferred to a 150 mL Erlenmeyer flask filled with 120 mL of an YEB liquid medium including a corresponding anti-biotic, and further cultivated overnight at 28° C. and 100 rpm until OD$_{600}$ was determined to be 0.85 to 0.9.

2. Bacterial solution collection: A bacterial solution in the Erlenmeyer flask was dispensed into two 50 mL centrifuge tubes and centrifuged at 5,000 rpm for 10 min, resulting supernatants were discarded, and resulting precipitates were suspended with 45 mL of CCM-liquid (1 L formula: 0.5 mL of 100×Fe salt (Na2-EDTA: 7.46 mg/L, and FeSO$_4$·7H$_2$O: 5.56 mg/L), 5 mL of 20×B5 mass (KNO$_3$: 50 g/L, NaH$_2$PO$_4$·2H$_2$O: 3 g/L, MgSO$_4$·7H$_2$O: 5 g/L, (NH$_4$) 2SO$_4$: 2.68 g/L, and CaCl$_2$·2H$_2$O: 3 g/L), 0.5 mL of 200×B5 trace (H$_3$BO$_3$: 0.6 g/L, MnSO$_4$·H$_2$O: 2 g/L, ZnSO$_4$·7H$_2$O: 0.4 g/L, KI: 0.15 g/L, Na2MoO$_4$·2H$_2$O: 0.05 g/L, CuSO$_4$·5H$_2$O: 0.05 g/L, and CoCl$_2$·6H$_2$O: 0.05 g/L), 10 mL of 100×B5 organic (niacin: 0.1 g/L, VB1: 1 g/L, VB6: 0.1 g/L, and creatine: 10 g/L), 30 g of sucrose (Qingdao MDBio, Inc.), and 3.9 g of MES (Qingdao MDBio, Inc.)). A resulting suspension was poured into a collection tank and then diluted with 45 mL of CCM-liquid, and when OD$_{600}$ of a bacterial solution in the collection tank was determined to be 0.5 to 0.6, the bacterial solution was placed in a refrigerator for later use.

3. Genetic transformation of cotyledonary nodes: Full *Glycine max* seeds with a uniform color and without cracks were selected and sterilized. A chlorine gas produced by a chemical reaction of HCl (concentrated)+NaClO→Cl$_2$↑+NaOH (a volume ratio of concentrated hydrochloric acid to sodium hypochlorite was 1:10) was used for sterilization, and the sterilization was conducted in a fume hood for 6.5 h. After the sterilization was completed, the seeds were placed on a clean bench to fully blow away the residual chlorine gas, and then the seeds were inserted into an SG4 solid medium (Qingdao MDBio, Inc.) by tweezers and cultivated overnight. A scalpel was first used to divide a swelled seed into two parts along a middle of a cotyledon, a true leaf was removed, and several wounds were gently created on a cotyledonary node along a direction of a hypocotyl. Treated explants and the bacterial suspension obtained in step 2) together were poured into a sterilized jar, and co-cultivated for 40 min at 28° C. and 120 rpm. Finally, the explants were taken out and placed on a filter paper on a CCM solid medium (which was obtained by adding agarose at 5 g/L on the basis of the CCM-liquid formula) with a cotyledonary node side facing downwards, where 14 explants were placed in each petri dish and cultivated for 5 d at 25° C. in the dark. Explants co-cultivated for 5 d were sterilized with sterilized water and Wash-Liquid, an excess part of each hypocotyl was cut off with 5 mm to 10 mm left, and then treated explants were obliquely inserted into an SIM solid medium (1 L formula: 5 mL of 100×Fe salt (Na2-EDTA: 7.46 mg/L, and FeSO$_4$·7H$_2$O: 5.56 mg/L), 50 mL of 20×B5 mass (KNO$_3$: 50 g/L, NaH$_2$PO$_4$·2H$_2$O: 3 g/L, MgSO$_4$·7H$_2$O: 5 g/L, (NH$_4$)$_2$SO$_4$: 2.68 g/L, and CaCl$_2$·2H$_2$O: 3 g/L), 5 mL of 200×B5 trace (H$_3$BO$_3$: 0.6 g/L, MnSO$_4$·H$_2$O: 2 g/L, ZnSO$_4$·7H$_2$O: 0.4 g/L, KI: 0.15 g/L, Na$_2$MoO$_4$·2H$_2$O: 0.05 g/L, CuSO$_4$·5H$_2$O: 0.05 g/L, and CoCl$_2$·6H$_2$O: 0.05 g/L), 10 mL of 100×B5 organic (niacin: 0.1 g/L, VB1: 1 g/L, VB6: 0.1 g/L, and creatine: 10 g/L), 30 g of sucrose (Qingdao MDBio, Inc.), 0.58 g of MES (Qingdao MDBio, Inc.), and 3.5 g of plant gel) with a growing point at an upward angle of 45°, where herbicide resistance screening was not conducted at this time, and 8 explants were inserted in each petri dish; the explants were cultivated at 26° C. under light for 15 d, and then a large bud and a part of a hypocotyl were removed; explants in which a cluster bud grew were transferred into an SIM solid medium with 6 mg/L glufosinate for screening and further cultivated for half a month, then cotyledons, dead leaves, and partial hypocotyls of incompletely-withered explants were removed, and the explants were transferred into an SEM solid medium with 4 mg/L glufosinate (1 L formula: 4.74 g of MS powder (Qingdao MDBio, Inc.), 5 mL of 100×Fe salt (Na2-EDTA: 7.46 mg/L, and FeSO4·7H$_2$O: 5.56 mg/L), 10 mL of 100×B5 organic (niacin: 0.1 g/L, VB1: 1 g/L, VB6: 0.1 g/L, and creatine: 10 g/L), 30 g of sucrose (Qingdao MDBio, Inc.), 0.58 g of MES (Qingdao MDBio, Inc.), and 3.5 g of plant gel) and cultivated, where the SEM medium was changed every half a month until buds were elongated; when a bud of an explant was elongated to 6 cm, a bottom was cut off, a cross-shaped wound was created at a stem bottom, and the explant was transferred into an RM rooting medium (1 L formula: 4.74 g of MS powder (Qingdao MDBio, Inc.), 2.5 mL of 100×Fe salt (Na2-EDTA: 7.46 mg/L, and FeSO4·7H$_2$O: 5.56 mg/L), 5 mL of 100×B5 organic (niacin: 0.1 g/L, VB1: 1 g/L, VB6: 0.1 g/L, and creatine: 10 g/L), 20 g of sucrose (Qingdao MDBio, Inc.), 0.58 g of MES (Qingdao MDBio, Inc.), and 3.5 g of plant gel) and cultivated for 10 d until an induced root was observed; and when a length of a root reached 5 cm or more, a tissue culture seedling was separated from a medium, transferred into a sterilized soil, and cultivated in an artificial incubator (16 h light/8 h dark, 25° C.).

5) Identification of Positive Transgenic Plants

Figure 5A:
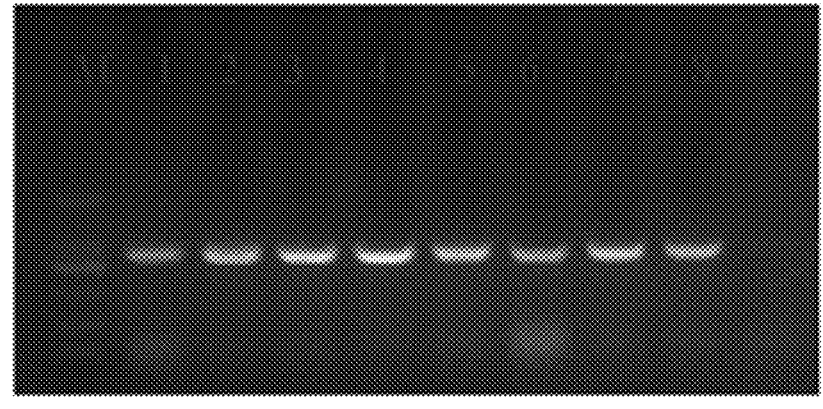
FIGS. 5A-5B show PCR detection results of a GmSAMMT transgenic material.

1. Overexpressed or knockout tissue culture seedlings transplanted into a soil were first tested for a bar gene. Test results are shown in FIG. 5A with lanes M, 1, 2, 3, 4, 5, 6, 7, and 8 from left to right, where lanes 1 to 3 represent KO_#1 knockout lines; lanes 4 to 6 represent KO_#2 knockout lines; and lanes 7 and 8 represent overexpressed lines denoted as OE_#1 and OE_#4 for subsequent experiments.

Figure 5B:

2. After the test, DNA was extracted from leaves of an overexpressed tissue culture seedling. A Vazyme® polymerase (2×Rapid Taq Master Mix) was used to conduct PCR identification with a 20.0 μL PCR system including the following components: 10 μL of 2×Rapid Taq Master Mix, 2 μL of Primer 1 (10 μM), 2 μL of Primer 2 (10 μM), 2 μL of Template DNA/cDNA, and the balance of ddH$_2$O. A PCR procedure was as follows: pre-denaturation at 95° C. for 3 min; denaturation at 95° C. for 15 s, renaturation at 60° C. for 15 s, and extension at 72° C. for 5 s, with 35 cycles in total; and thorough extension at 72° C. for 5 min. A left primer for the PCR was located in a promoter region of a vector 35, and a right primer for the PCR was located downstream of a gene coding region (the left primer was shown in SEQ ID NO: 21 and the right primer was shown in SEQ ID NO: 10). A seedling with a desired band size and a completely-correct sequence was determined as a positive overexpressed seedling. PCR identification results are shown in FIG. 5B with lanes M, 1, 2, 3, 4, and 5 from left to right, where M represents DL2000; lanes 1 to 3 represent overexpressed lines OE_#1; and lanes 4 and 5 represent overexpressed lines OE_#4.

Figure 6A:
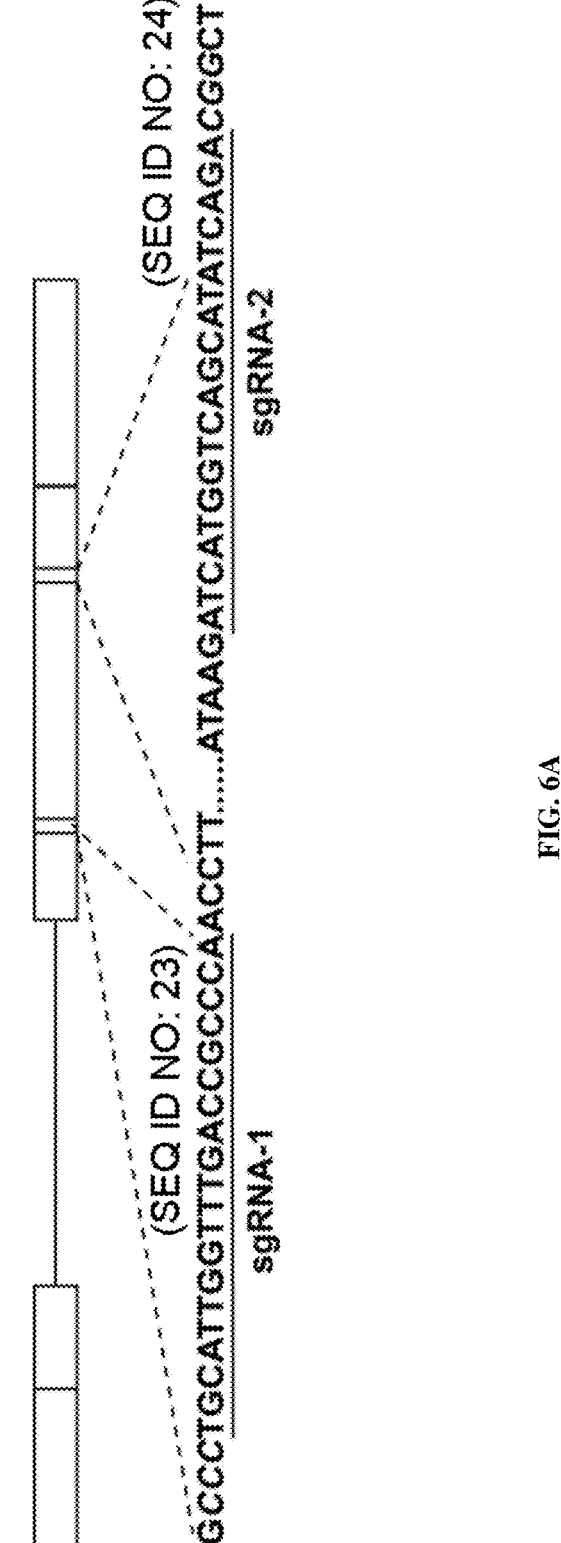

3. A positive knockout seedling was tested using a high-fidelity enzyme of Vazyme® (Phanta® Max Super-Fidelity DNA Polymerase) with a 50 μL PCR system including the following components: 2 μL of a template, 2 μL of each of upstream and downstream primers, 1 μL of dNTP Mix, 25 μL of 2×Phanta Max Buffer, 1 μL of Phanta Max Super-Fidelity DNA Polymerase, and the balance of ddH$_2$O. A PCR procedure was as follows: pre-denaturation at 95° C. for 3 min; denaturation at 95° C. for 15 s, annealing at 58° C. for 15 s, and extension at 72° C. for 15 s, with 35 cycles in total; and finally, thorough extension at 72° C. for 5 min. Primers used for the PCR were shown in SEQ ID NO: 19 and SEQ ID NO: 20, respectively. A sequencing result of the positive knockout seedling was compared with a sequencing result of a control material Jack. Homozygotes and editing types are shown in FIGS. 6A-6B, where FIG. 6A shows a structure of the GmSAMMT gene and positions of targets sgRNA-1 and sgRNA-2, where a black region represents CDS, a gray region represents an untranslated region (UTR), and a black straight line represents an intron region; and FIG. 6B shows editing types of GmSAMMT-knockout transgenic materials, where an italicized region represents an NGG sequence, an underscored region represents a 20 bp target sequence, and a dotted line represents a missed base sequence.

4. qRT-PCR was used to detect a transcription level of the target gene in a transgenic material with primers shown in SEQ ID NO: 5 and SEQ ID NO: 6, respectively. An expression level of the target gene in each of the control material Jack and two knockout materials was determined, and four parallel replicates were set for each material. An expression level of the target gene in each of the control material Jack and two overexpressed materials was determined, and three parallel replicates were set for each material. A 20.0 μL qRT-PCR system was as follows: 10 μL of 2×ChamQ SYBRqPCR Master Mix, 0.4 μL of Primer 1 (10 μM), 0.4 μL of Primer 2 (10 μM), 0.4 μL of 50×ROX Reference Dye 1, 5 μL of Template DNA/cDNA, and the balance of ddH$_2$O. A qRT-PCR reaction procedure was as follows: pre-denaturation at 95° C. for 30 s; and denaturation at 95° C. for 10 s and extension at 60° C. for 30 s, with 40 cycles in total. A dissolution curve involved dissolution at 95° C. for 15 s, dissolution at 60° C. for 1 min, and dissolution at 95° C. for 15 s. Results are shown in FIGS. 7A-7B and Table 1, where a represents an expression level of the GmSAMMT gene in each of the control material Jack and the two knockout materials, and N=4; b represents an expression level of the GmSAMMT gene in each of the control material Jack and the two overexpressed materials, and N=3; an error bar represents mean±SD, and a two-tailed T-test is adopted for statistical analysis; *, P<0.05; , P<0.01; and *, P<0.001.

TABLE 1

| | | Test results of transcription levels of GmSAMMT in transgenic *Glycine max* materials | | | | |
|---|---|---|---|---|---|---|
| | Jack | KO__#1 | KO__#2 | Jack | OE__#1 | OE__#4 |
| Replicate 1 | 1.35835 | 0.09706 | 0.05125 | 1.30381 | 5.34126 | 16.78689 |
| Replicate 2 | 1.37237 | 0.08151 | 0.05508 | 1.29845 | 4.58454 | 18.22623 |
| Replicate 3 | 1.00000 | 0.04902 | 0.09598 | 1.18138 | 5.77766 | 16.92747 |
| Replicate 4 | 1.58059 | 0.10912 | 0.05332 | — | — | — |
| Mean | 1.33 | 0.08 | 0.06 | 1.26 | 5.23 | 17.31 |

Figure 7A:
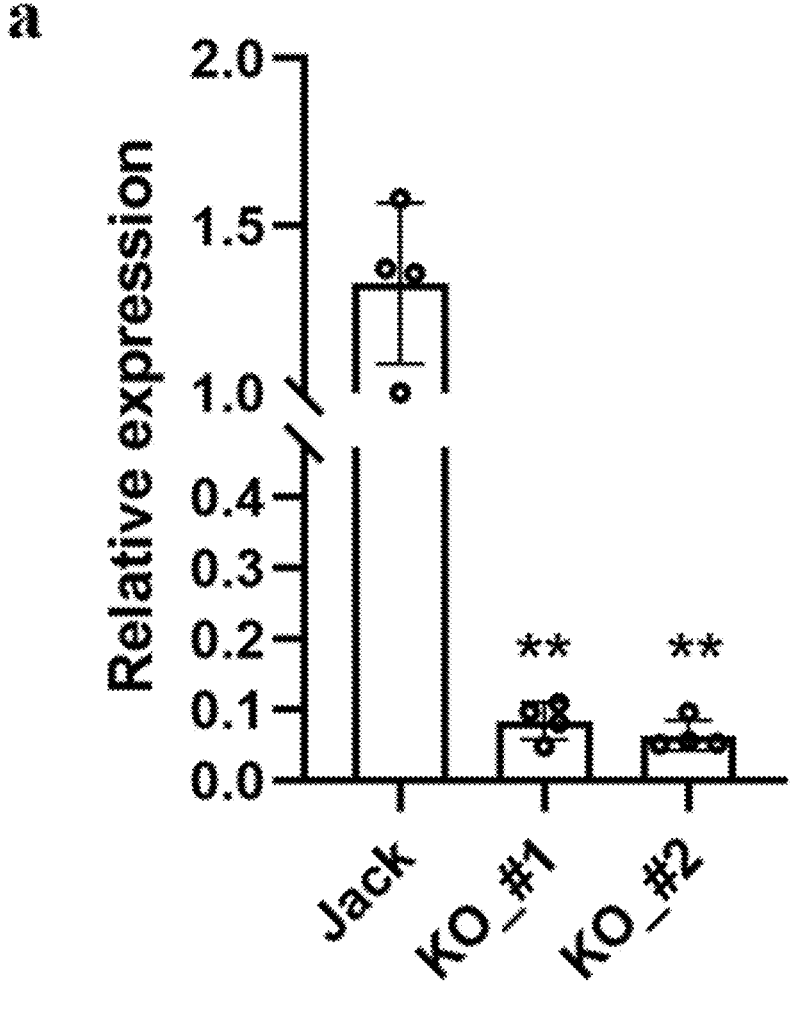
FIGS. 7A-7B show detection results of transcription levels of GmSAMMT in transgenic *Glycine max* lines.
Figure 7B:
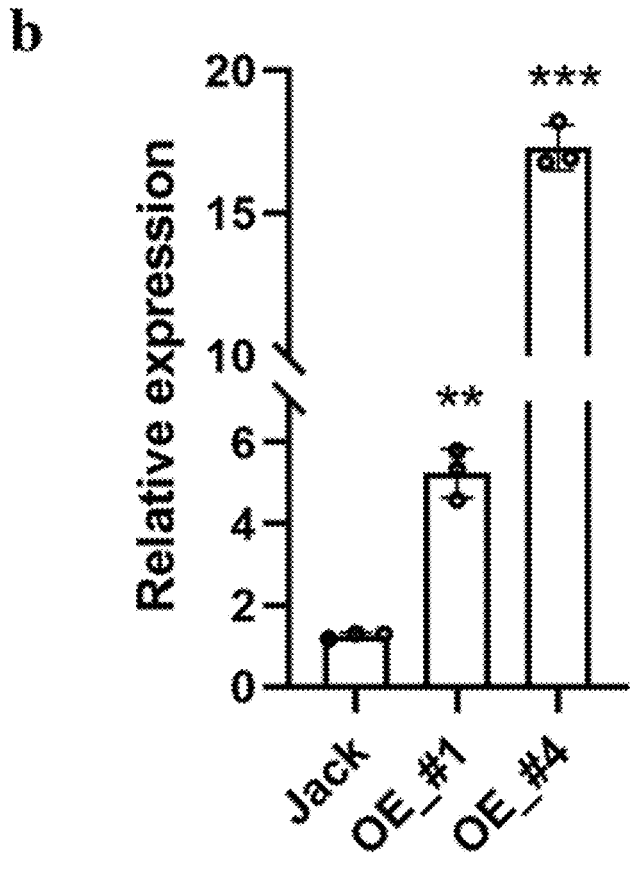

It can be seen from FIGS. 7A-7B and Table 1 that, compared with the control material Jack, an expression level of the target gene in an overexpressed material is significantly increased (N=3) (FIG. 7B), and an expression level of the target gene in a knockout material is significantly decreased (N=4) (FIG. 7A).

6) Determination of Protein Contents in Mature Seeds of Transgenic Plants

A protein content in mature seeds of each of the plants control Jack, KO_#1, KO_#2, OE_#1, and OE_#4 was determined, and 3 parallel replicates were set for each plant. A method for determining the protein content was a Kjeldahl nitrogen determination method recommended in the national standard GB/T 5511-2008, and an instrument for determining the protein content was a Kjeltec8400 automatic Kjeldahl nitrogen determination instrument (FOSS). Results are shown in FIGS. 8A-8B and Table 2, where a shows protein contents of the Jack and the two GmSAMMT-knockout transgenic lines; and b shows protein contents of the Jack and the two GmSAMMT-overexpressed transgenic lines.

TABLE 2

| | | Test results of protein contents in seeds of GmSAMMT transgenic *Glycine max* materials (g/100 g of seeds) | | | |
|---|---|---|---|---|---|
| | Jack | KO__#1 | KO__#2 | OE__#1 | OE__#4 |
| Replicate 1 | 34.6614 | 42.9167 | 38.0003 | 33.0741 | 32.7372 |
| Replicate 2 | 34.6551 | 43.5086 | 38.0879 | 33.2116 | 32.7659 |
| Replicate 3 | 34.6868 | 45.2000 | 38.1710 | 32.8557 | 32.2274 |
| Mean | 34.67 | 43.88 | 38.09 | 33.05 | 32.58 |

Figure 8A:
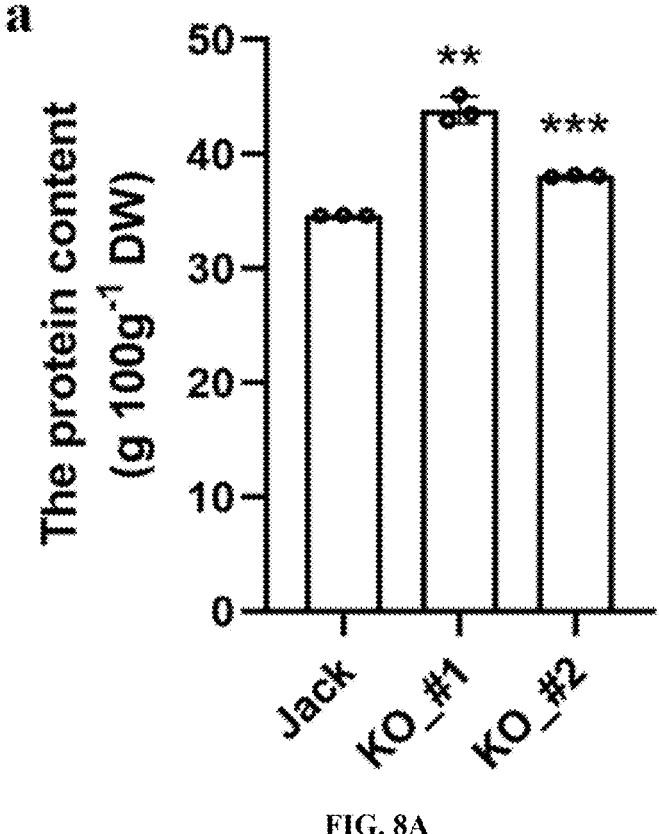
FIGS. 8A-8B show protein contents in seeds of GmSAMMT transgenic *Glycine max* materials.
Figure 8B:
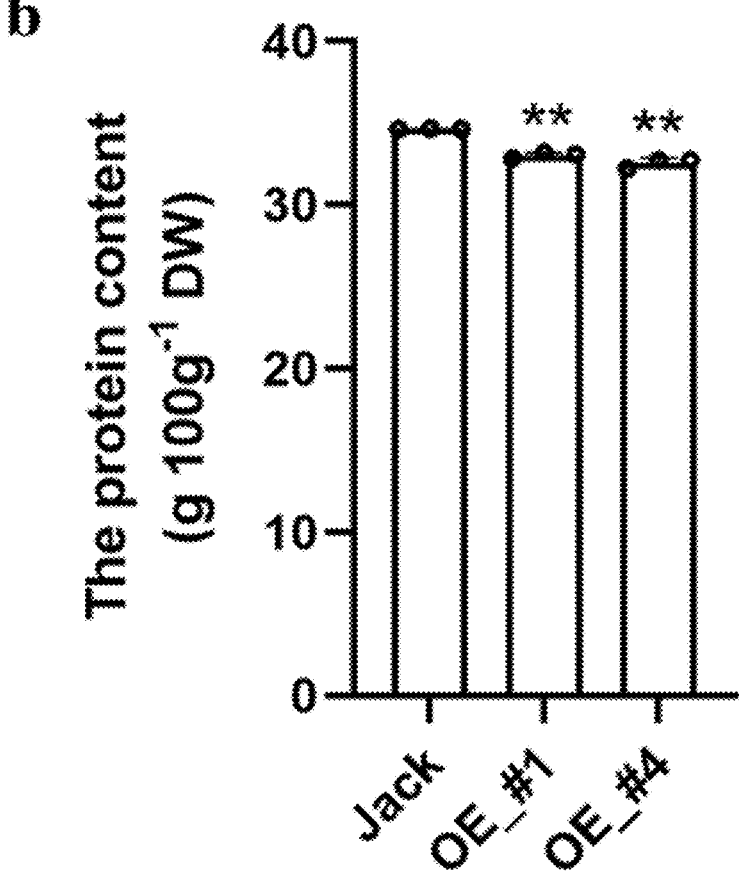
Figure 9A:
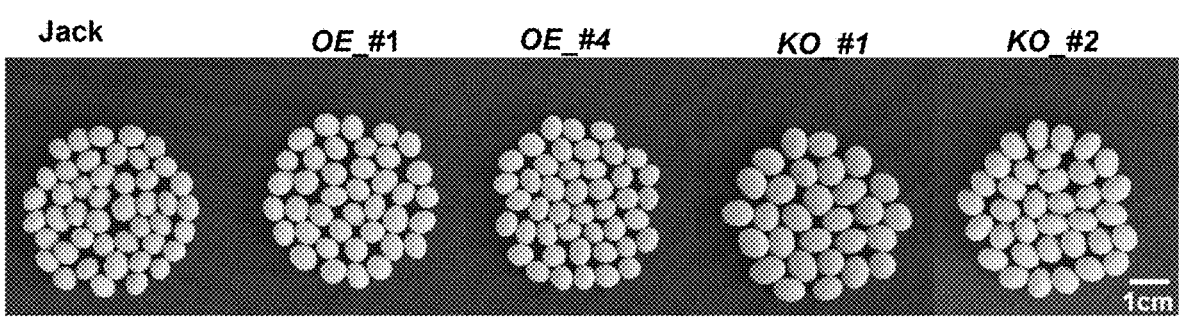
FIGS. 9A-9I show detection results of seed phenotypes, 100-seed weights, seed lengths, seed widths, and seed thicknesses of GmSAMMT transgenic *Glycine max* materials.
Figure 9B:
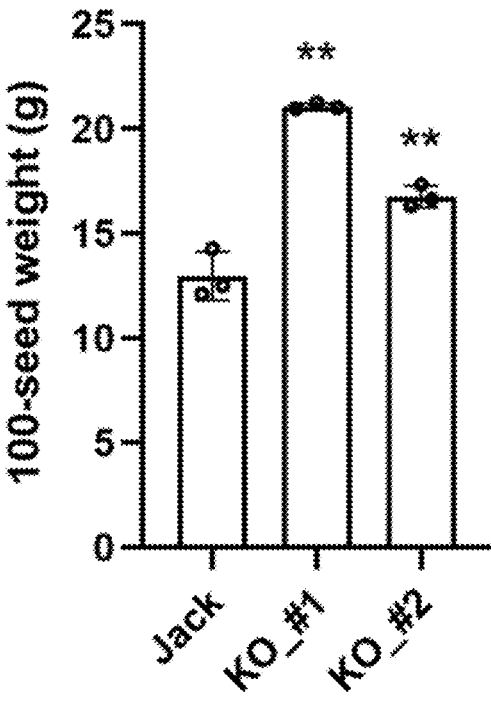
Figure 9C:
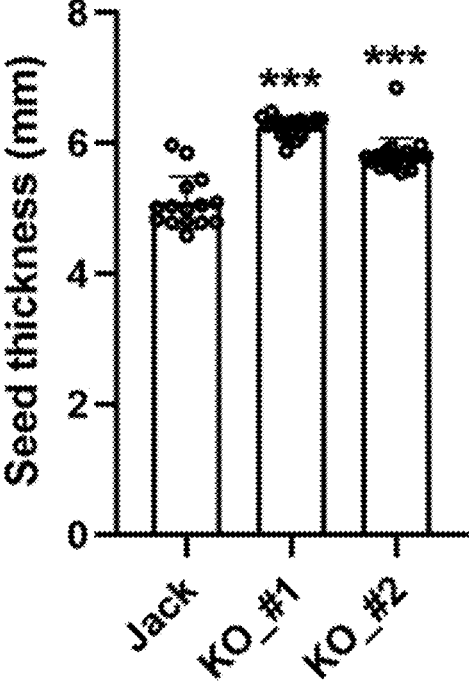
Figure 9D:
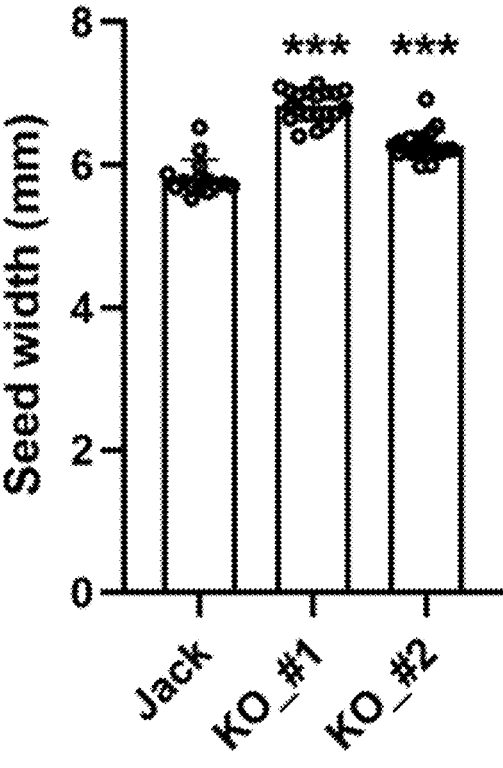
Figure 9E:
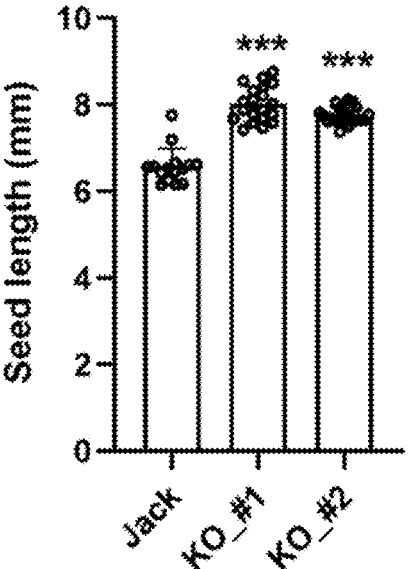
Figure 9F:
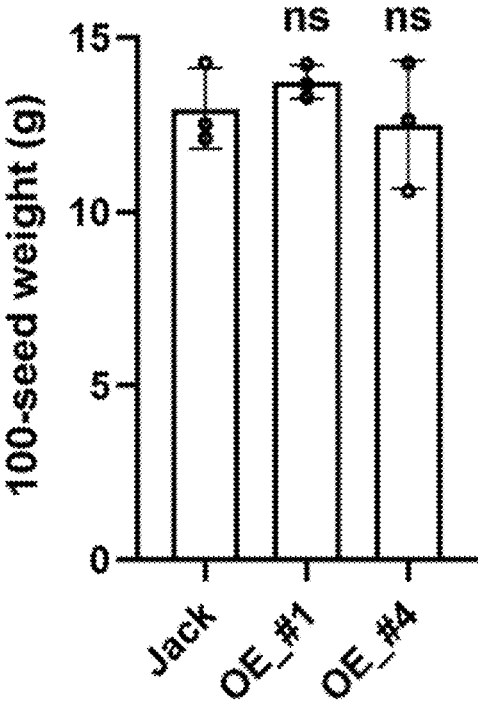
Figure 9G:
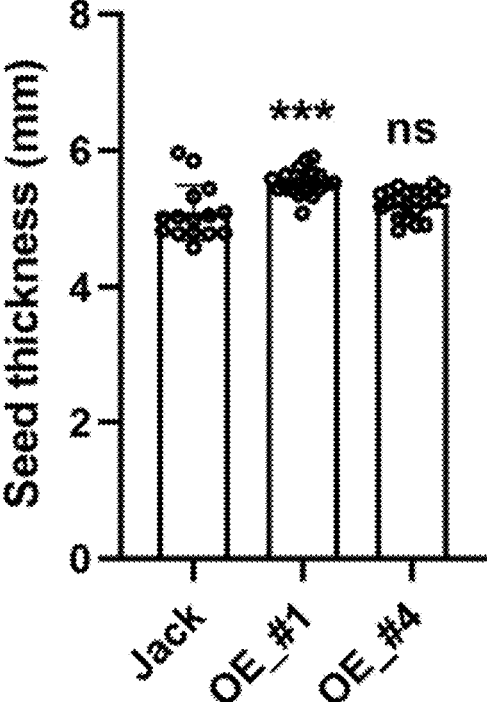
Figure 9H:
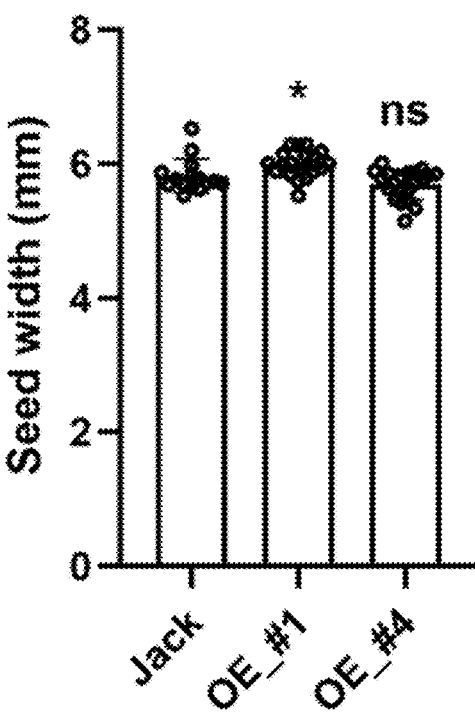
Figure 9I:
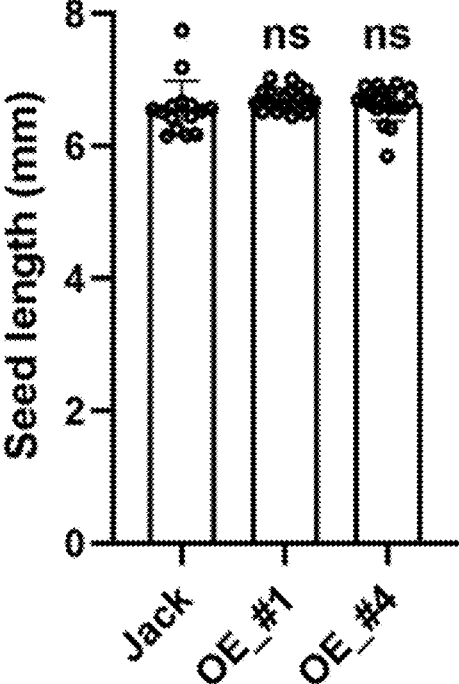

It can be seen from FIGS. 8A-8B and Table 2 that, compared with the control material, protein contents in seeds of the two knockout materials both are significantly increased (N=3) (FIG. 8A), and in contrast, protein contents in seeds of the two overexpressed materials both are significantly decreased (N=3) (FIG. 8B). The above results show that the GmSAMMT gene can negatively regulate a protein content of *Glycine max*, and the knockout of this gene can significantly increase a protein content in seeds of *Glycine max*, thereby improving a nutritional quality of *Glycine max*.

7) Determination of Seed Weights of Transgenic Materials

Harvested transgenic *Glycine max* seeds were dried in an oven at 37° C. for one week, and then the traits such as 100-seed weight (N=3), seed length (N>15), seed width (N>15), and seed thickness (N>15) of the control material Jack and the transgenic materials were determined. Results are shown in FIGS. 9A-9I and Tables 3 to 6, where a shows seed phenotypes of the Jack and GmSAMMT-edited transgenic lines; b shows the comparison of seed weights, seed lengths, seed thicknesses, and seed widths of the Jack and GmSAMMT-edited transgenic lines; c shows the comparison of seed weights, seed lengths, seed thicknesses, and seed widths of the Jack and GmSAMMT-overexpressed transgenic lines; three parallel replicates are set for the seed weight trait (N=3); and more than fifteen replicates are set for the seed length, seed thickness, and seed width traits (N>15) (specific details are shown in the tables below).

TABLE 3

| | | 100-seed weights of the control material Jack and the transgenic materials (g) | | | |
|---|---|---|---|---|---|
| | Jack | KO__#1 | KO__#2 | OE__#1 | OE__#4 |
| Replicate 1 | 12.5154 | 21.2414 | 17.3457 | 14.2447 | 12.6310 |
| Replicate 2 | 12.1200 | 21.0000 | 16.6260 | 13.6630 | 14.2820 |
| Replicate 3 | 14.2850 | 20.9753 | 16.3260 | 13.2960 | 10.6080 |
| Mean | 12.97 | 21.07 | 16.77 | 13.73 | 12.51 |

TABLE 4

| | | Seed thicknesses of the control material Jack and the transgenic materials (mm) | | | |
|---|---|---|---|---|---|
| | Jack | KO__#1 | KO__#2 | OE__#1 | OE__#4 |
| Replicate 1 | 5.0100 | 5.8800 | 6.8500 | 5.5100 | 5.0000 |
| Replicate 2 | 4.7800 | 6.3500 | 5.7700 | 5.4600 | 5.5200 |
| Replicate 3 | 5.3300 | 6.3000 | 5.6800 | 5.5200 | 5.2300 |
| Replicate 4 | 5.4400 | 6.2600 | 5.8000 | 5.7600 | 5.4800 |
| Replicate 5 | 5.8500 | 6.2800 | 5.7900 | 5.9100 | 5.1700 |
| Replicate 6 | 4.9800 | 6.1400 | 5.7900 | 5.5200 | 5.2900 |
| Replicate 7 | 5.0300 | 6.1100 | 5.9700 | 5.6400 | 5.3900 |
| Replicate 8 | 5.0900 | 6.4800 | 5.8100 | 5.0800 | 5.2300 |
| Replicate 9 | 5.9700 | 6.3800 | 5.6800 | 5.6500 | 5.1400 |
| Replicate 10 | 4.8000 | 6.0800 | 5.8800 | 5.4400 | 4.9000 |
| Replicate 11 | 4.5800 | 6.3200 | 5.6900 | 5.3500 | 5.3900 |
| Replicate 12 | 4.7800 | 6.3200 | 5.9300 | 5.5500 | 4.8300 |
| Replicate 13 | 5.0500 | 6.4000 | 5.8100 | 5.8700 | 4.9100 |
| Replicate 14 | 4.8300 | 6.2800 | 5.5900 | 5.3900 | 5.4100 |
| Replicate 15 | 4.7900 | 6.3500 | 5.6900 | 5.6700 | 5.2000 |
| Replicate 16 | — | 6.3600 | 5.5400 | 5.5800 | 5.2900 |
| Replicate 17 | — | 6.1400 | 5.6200 | 5.4300 | 5.4100 |
| Replicate 18 | — | 6.2700 | 5.8700 | 5.5300 | 5.4200 |
| Replicate 19 | — | 6.2900 | 5.8100 | 5.3300 | 4.9800 |
| Replicate 20 | — | 6.0300 | 5.7200 | 5.4800 | 5.3600 |
| Replicate 21 | — | — | 5.8000 | — | — |
| Mean | 5.09 | 6.25 | 5.81 | 5.53 | 5.23 |

TABLE 5

| | | Seed widths of the control material Jack and the transgenic materials (mm) | | | |
|---|---|---|---|---|---|
| | Jack | KO__#1 | KO__#2 | OE__#1 | OE__#4 |
| Replicate 1 | 5.7800 | 6.4700 | 6.1300 | 6.0100 | 5.6200 |
| Replicate 2 | 5.6900 | 6.8100 | 6.3200 | 5.8900 | 6.0200 |
| Replicate 3 | 5.9800 | 6.7200 | 6.2100 | 5.9800 | 5.8100 |
| Replicate 4 | 5.8800 | 6.7100 | 6.2000 | 6.1300 | 5.8500 |
| Replicate 5 | 6.2000 | 6.7700 | 6.1900 | 6.3000 | 5.4200 |
| Replicate 6 | 5.7700 | 6.4000 | 6.2100 | 5.9400 | 5.6400 |
| Replicate 7 | 5.7100 | 7.0000 | 6.3200 | 6.1500 | 5.8700 |
| Replicate 8 | 5.7200 | 7.0400 | 6.2200 | 5.5300 | 5.7700 |
| Replicate 9 | 6.5300 | 7.0900 | 6.2500 | 5.7900 | 5.7200 |
| Replicate 10 | 5.7000 | 6.6500 | 6.2000 | 6.1900 | 5.6300 |
| Replicate 11 | 5.8200 | 6.9800 | 6.1600 | 5.8400 | 5.8900 |
| Replicate 12 | 5.6600 | 7.1400 | 6.4700 | 6.0100 | 5.3400 |
| Replicate 13 | 5.7400 | 7.0200 | 6.3700 | 6.3000 | 5.1500 |
| Replicate 14 | 5.6200 | 7.0200 | 6.2700 | 5.9500 | 5.9300 |
| Replicate 15 | 5.5300 | 7.0300 | 6.1800 | 6.2800 | 5.8500 |
| Replicate 16 | — | 6.9700 | 6.0000 | 5.8900 | 5.8300 |
| Replicate 17 | — | 6.7200 | 5.9800 | 6.1300 | 5.7900 |
| Replicate 18 | — | 6.8000 | 6.2400 | 6.0100 | 5.8800 |
| Replicate 19 | — | 6.7100 | 6.5500 | 5.9100 | 5.4400 |

TABLE 5-continued

| | Seed widths of the control material Jack and the transgenic materials (mm) | | | | |
|---|---|---|---|---|---|
| | Jack | KO_#1 | KO_#2 | OE_#1 | OE_#4 |
| Replicate 20 | — | 6.5600 | 6.9200 | 5.7400 | 5.4700 |
| Replicate 21 | — | — | 6.3500 | — | — |
| Mean | 5.82 | 6.83 | 6.27 | 6.00 | 5.70 |

TABLE 6

| | Seed lengths of the control material Jack and the transgenic materials (mm) | | | | |
|---|---|---|---|---|---|
| | Jack | KO_#1 | KO_#2 | OE_#1 | OE_#4 |
| Replicate 1 | 6.5300 | 7.5900 | 7.8100 | 6.6600 | 6.6200 |
| Replicate 2 | 6.4300 | 7.4200 | 7.9500 | 6.4500 | 6.9200 |
| Replicate 3 | 6.5600 | 7.6800 | 7.9300 | 6.5300 | 6.2700 |
| Replicate 4 | 6.6200 | 7.5900 | 7.6500 | 6.4900 | 6.8100 |
| Replicate 5 | 7.7500 | 7.6900 | 7.6200 | 6.6600 | 6.5800 |
| Replicate 6 | 6.6100 | 7.4700 | 7.6600 | 7.0300 | 6.6200 |
| Replicate 7 | 6.1800 | 8.0800 | 7.7800 | 6.8400 | 6.7300 |
| Replicate 8 | 6.6600 | 8.1200 | 8.0800 | 6.7100 | 6.5700 |
| Replicate 9 | 7.1900 | 8.5000 | 7.5000 | 6.8400 | 6.7200 |
| Replicate 10 | 6.5700 | 8.7600 | 7.8100 | 6.6400 | 6.7000 |
| Replicate 11 | 6.2500 | 8.6300 | 7.7500 | 6.5200 | 6.9100 |
| Replicate 12 | 6.5200 | 8.3300 | 7.3800 | 6.7600 | 5.8500 |
| Replicate 13 | 6.4500 | 8.0200 | 7.6200 | 6.6600 | 6.3100 |
| Replicate 14 | 6.1600 | 8.2100 | 7.6500 | 6.5200 | 6.9400 |
| Replicate 15 | 6.1500 | 8.4200 | 8.1200 | 6.9000 | 6.5800 |
| Replicate 16 | — | 7.8900 | 7.6500 | 6.6500 | 6.7800 |
| Replicate 17 | — | 7.8800 | 8.0600 | 6.8300 | 6.8700 |
| Replicate 18 | — | 7.7900 | 7.7300 | 7.0200 | 6.8200 |
| Replicate 19 | — | 7.7900 | 7.6400 | 6.6000 | 6.5900 |

TABLE 6-continued

| | Seed lengths of the control material Jack and the transgenic materials (mm) | | | | |
|---|---|---|---|---|---|
| | Jack | KO_#1 | KO_#2 | OE_#1 | OE_#4 |
| Replicate 20 | — | 8.5500 | 7.6900 | 6.8300 | 6.6700 |
| Replicate 21 | — | — | 7.5700 | — | — |
| Mean | 6.58 | 8.02 | 7.75 | 6.71 | 6.64 |

It can be seen from FIGS. 9A-9I and Tables 3 to 6 that, compared with the control material Jack, mature seeds of the transgenic materials show no significant difference in terms of appearance (FIG. 9A), but the seed weights, seed lengths, seed widths, and seed thicknesses of the transgenic materials are significantly increased (FIGS. 9B-9E). Although a seed weight of an overexpressed line is decreased compared with the control material Jack, there is no significant difference. The above results show that the GmSAMMT gene can negatively regulate a seed weight of *Glycine max*.

In summary, the *Glycine max* GmSAMMT gene can negatively regulate a seed weight and a protein content of *Glycine max*, and the knockout of the GmSAMMT gene can improve the yield and quality traits of *Glycine max*. Therefore, the GmSAMMT gene can be used in improvement of a nutritional quality of *Glycine max*.

The present disclosure has been disclosed with preferred examples as above, which shall not be construed as a limitation to the present disclosure. Any person skilled in the art can make changes and variations without departing from the spirit and scope of the present disclosure. The present disclosure shall fall within the protection scope defined in the claims.

What is claimed is:

1. A method for breeding a transgenic *Glycine max* plant, comprising constructing a recombinant vector for knockout of a GmSAMMT gene; and transforming the recombinant vector into a *Glycine max* plant to obtain the transgenic *Glycine max* plant; wherein the protein encoded by the GmSAMMT gene has the amino acid sequence of SEQ ID NO: 1 and the transgenic *Glycine max* plant has a higher seed protein content and higher yield than those of a control plant.

*     *     *     *     *

SEQUENCE LISTING

```
Sequence total quantity: 30
SEQ ID NO: 1            moltype = AA  length = 261
FEATURE                 Location/Qualifiers
source                  1..261
                        mol_type = protein
                        note = protein encoded by GmSAMMT gene
                        organism = Glycine max
SEQUENCE: 1
MAKLFLKQAK QYADARPSYP PQLFQFIASK TPSHNLAWDV GTGSGQAAKS LAAIYKNVIA  60
TDASDKQLEF AAKLPNVRYQ HTPSTMSTAE LEQMVASKGT IDLVTIAQAL HWFDRPTFYE  120
QVKWVLKKPH GIIAAWCYYL PRVSDAFDTV FDQFYSTNVS PYWDPARKWV DDNYRSIDFP  180
FEPVDGADHT GPFEFVTETM MDLDDFLTYI RSWSAYQTAK EKGVELLAED VVEKFKLAWG  240
EDAKKVVKFP IYLRIGRTGD S                                           261

SEQ ID NO: 2            moltype = DNA  length = 1226
FEATURE                 Location/Qualifiers
source                  1..1226
                        mol_type = genomic DNA
                        note = GmSAMMT gene
                        organism = Glycine max
CDS                     138..923
                        protein_id = 22
                        translation = MAKLFLKQAKQYADARPSYPPQLFQFIASKTPSHNLAWDVGTGSGQ
                        AAKSLAAIYKNVIATDASDKQLEFAAKLPNVRYQHTPSTMSTAELEQMVASKGTIDLVT
                        IAQALHWFDRPTFYEQVKWVLKKPHGIIAAWCYYLPRVSDAFDTVFDQFYSTNVSPYWD
                        PARKWVDDNYRSIDFPPFEPVDGADHTGPFEFVTETMMDLDDFLTYIRSWSAYQTAKEKG
                        VELLAEDVVEKFKLAWGEDAKKVVKFPIYLRIGRTGDS
SEQUENCE: 2
ttcaggacgc aacgggggtg atggcatcat ggttattaca gaataaatga ttgaagagtg  60
atggaaggtt cttgcttttg tttgtatata tacatactat tattgctagg aaattgaaga  120
cctaagatac aatagagatg gcaaagctat ttttgaaaca ggcaaagcaa tacgcagatg  180
caagaccaag ctatcctcca caactcttcc aattcattgc ttccaagact ccctctcaca  240
acctcgcttg ggacgtcggc actgggagcg gccaagctgc caaatcttta gctgcaatat  300
acaagaatgt gatagccaca gatgctagtg acaaacaact tgaatttgca gccaagctcc  360
caaatgtgag ataccaacac accccttcaa ccatgtcgac ggccgagctt gaacaaatgg  420
tggcatctaa gggaaccata gaccttgtga ccatagcaca agccctgcat tggtttgacc  480
```

```
gcccaacctt ctacgaacaa gtgaagtggg ttctcaagaa acctcatgga atcattgctg    540
cttggtgtta ctatttgcca agagttagtg atgcatttga cactgtcttt gaccaattct    600
attccactaa tgtaagccct tattgggacc cagctcgtaa atgggttgat gacaattata    660
gaagcattga ttttccattt gagcccgtgg atggagctga tcacacagga ccctttgagt    720
ttgtgacgga aacaatgatg gatttggatg atttcttgac ctacataaga tcatggtcag    780
catatcagac ggctaaggag aaaggagtgg agcttctcgc ggaggatgtg gttgaaaaat    840
tcaagcttgc ttggggtgaa gatgctaaaa aagttgtcaa gtttccaatt tatttgagaa    900
ttggaagaac aggggattcc taaagacata tgcaaatggt tgcttttact gtgtgggaga    960
tgtgacgagt accaactttt atgagtttat ccattgattg aataatgtaa ttttattgaa   1020
ttgcgttcat gttaagtcaa aagcttttaa attcgaaggg tacaattcct acttatctgg   1080
aaagagttga gccttagttt gctatgttaa ttttgtaatt tggtattgat aaattttgtt   1140
gtgtgtgtca accaaatttt gatagaaaag tacttgtagt aaatacttga taatttattt   1200
taatgatgtt aaattaaggt atttgc                                        1226
```

```
SEQ ID NO: 3            moltype = DNA  length = 37
FEATURE                 Location/Qualifiers
source                  1..37
                        mol_type = other DNA
                        note = Upstream Primer for amplification of CDS of GmSAMMT
                          gene
                        organism = synthetic construct
SEQUENCE: 3
ggatcttcca gagatgtagt catggtagtc tgcacca                              37

SEQ ID NO: 4            moltype = DNA  length = 35
FEATURE                 Location/Qualifiers
source                  1..35
                        mol_type = other DNA
                        note = Downstream Primer for amplification of CDS of
                          GmSAMMT gene
                        organism = synthetic construct
SEQUENCE: 4
ctgccgttcg acgatactcg tcacatctcc cacac                                35

SEQ ID NO: 5            moltype = DNA  length = 20
FEATURE                 Location/Qualifiers
source                  1..20
                        mol_type = other DNA
                        note = Upstream primer for fluorescence quantification of
                          GmSAMMT
                        organism = synthetic construct
SEQUENCE: 5
gaatttgcag ccaagctccc                                                 20

SEQ ID NO: 6            moltype = DNA  length = 20
FEATURE                 Location/Qualifiers
source                  1..20
                        mol_type = other DNA
                        note = Downstream primer for fluorescence quantification of
                          GmSAMMT
                        organism = synthetic construct
SEQUENCE: 6
cagggcttgt gctatggtca                                                 20

SEQ ID NO: 7            moltype = DNA  length = 41
FEATURE                 Location/Qualifiers
source                  1..41
                        mol_type = other DNA
                        note = Upstream primer for intact CDS of the GmSAMMT gene
                          without a stop codon
                        organism = synthetic construct
SEQUENCE: 7
tacaaatcta tctctctcga gatggcaaag ctatttttga a                         41

SEQ ID NO: 8            moltype = DNA  length = 41
FEATURE                 Location/Qualifiers
source                  1..41
                        mol_type = other DNA
                        note = Downstream primer for intact CDS of the GmSAMMT gene
                          without a stop codon
                        organism = synthetic construct
SEQUENCE: 8
tgctcaccat ggatccccgg gggaatcccc tgttcttcca a                         41

SEQ ID NO: 9            moltype = DNA  length = 38
FEATURE                 Location/Qualifiers
source                  1..38
                        mol_type = other DNA
                        note = Upstream primer for cloning of an enzyme cleavage
```

-continued

```
                       site-containing sequence in GmSAMMT gene
                       organism = synthetic construct
SEQUENCE: 9
gggcccaggc ctacgcgtat ggcaaagcta tttttgaa                               38

SEQ ID NO: 10         moltype = DNA   length = 38
FEATURE               Location/Qualifiers
source                1..38
                      mol_type = other DNA
                      note = Downstream primer for cloning of an enzyme cleavage
                       site-containing sequence in GmSAMMT gene
                      organism = synthetic construct
SEQUENCE: 10
tcggggaaat tcgagctctt aggaatcccc tgttcttc                               38

SEQ ID NO: 11         moltype = DNA   length = 30
FEATURE               Location/Qualifiers
source                1..30
                      mol_type = other DNA
                      note = Upstream primer for a first amplification product
                      organism = synthetic construct
SEQUENCE: 11
catgccatgg tagaggagct gttctgcttc                                        30

SEQ ID NO: 12         moltype = DNA   length = 40
FEATURE               Location/Qualifiers
source                1..40
                      mol_type = other DNA
                      note = Downstream primer for a first amplification product
                      organism = synthetic construct
SEQUENCE: 12
tctgatatgc tgaccatgat tgaccagaca tgtcacgctt                             40

SEQ ID NO: 13         moltype = DNA   length = 40
FEATURE               Location/Qualifiers
source                1..40
                      mol_type = other DNA
                      note = Upstream primer for a second amplification product
                      organism = synthetic construct
SEQUENCE: 13
atcatggtca gcatatcaga gttttagagc tagaaatagc                             40

SEQ ID NO: 14         moltype = DNA   length = 29
FEATURE               Location/Qualifiers
source                1..29
                      mol_type = other DNA
                      note = Downstream primer for a second amplification product
                      organism = synthetic construct
SEQUENCE: 14
gtcagtcgac catgaatagg tctatgacc                                        29

SEQ ID NO: 15         moltype = DNA   length = 29
FEATURE               Location/Qualifiers
source                1..29
                      mol_type = other DNA
                      note = Upstream primer for a third amplification product
                      organism = synthetic construct
SEQUENCE: 15
gtcagtcgac ggaattgtga gcggataac                                        29

SEQ ID NO: 16         moltype = DNA   length = 40
FEATURE               Location/Qualifiers
source                1..40
                      mol_type = other DNA
                      note = Downstream primer for a third amplification product
                      organism = synthetic construct
SEQUENCE: 16
tgcattggtt tgaccgccca aatccatatg ttttcctggg                             40

SEQ ID NO: 17         moltype = DNA   length = 40
FEATURE               Location/Qualifiers
source                1..40
                      mol_type = other DNA
                      note = Upstream primer for a fourth amplification product
                      organism = synthetic construct
SEQUENCE: 17
tgggcggtca aaccaatgca gttttagagc tagaaatagc                             40

SEQ ID NO: 18         moltype = DNA   length = 30
```

-continued

```
FEATURE               Location/Qualifiers
source                1..30
                      mol_type = other DNA
                      note = Downstream primer for a fourth amplification product
                      organism = synthetic construct
SEQUENCE: 18
ctagtctaga ccatgaatag gtctatgacc                                     30

SEQ ID NO: 19         moltype = DNA  length = 22
FEATURE               Location/Qualifiers
source                1..22
                      mol_type = other DNA
                      note = Upstream primer for sequencing of GmSAMMT knockout
                       vector
                      organism = synthetic construct
SEQUENCE: 19
agcattgtct ctgcctctta ac                                             22

SEQ ID NO: 20         moltype = DNA  length = 21
FEATURE               Location/Qualifiers
source                1..21
                      mol_type = other DNA
                      note = Downstream primer for sequencing of GmSAMMT knockout
                       vector
                      organism = synthetic construct
SEQUENCE: 20
cgtcacatct cccacacagt a                                              21

SEQ ID NO: 21         moltype = DNA  length = 16
FEATURE               Location/Qualifiers
source                1..16
                      mol_type = other DNA
                      note = Left primer for  identification of positive
                       transgenic plant
                      organism = synthetic construct
SEQUENCE: 21
atgacgcaca atccca                                                    16

SEQ ID NO: 22         moltype = AA  length = 261
FEATURE               Location/Qualifiers
source                1..261
                      mol_type = protein
                      note = Amino acid sequence encoded by CDS of GmSAMMT
                      organism = Glycine max
SEQUENCE: 22
MAKLFLKQAK QYADARPSYP PQLFQFIASK TPSHNLAWDV GTGSGQAAKS LAAIYKNVIA 60
TDASDKQLEF AAKLPNVRYQ HTPSTMSTAE LEQMVASKGT IDLVTIAQAL HWFDRPTFYE 120
QVKWVLKKPH GIIAAWCYYL PRVSDAFDTV FDQFYSTNVS PYWDPARKWV DDNYRSIDFP 180
FEPVDGADHT GPFEFVTETM MDLDDFLTYI RSWSAYQTAK EKGVELLAED VVEKFKLAWG 240
EDAKKVVKFP IYLRIGRTGD S                                             261

SEQ ID NO: 23         moltype = DNA  length = 30
FEATURE               Location/Qualifiers
source                1..30
                      mol_type = other DNA
                      note = sgRNA-1 targeted gene fragment
                      organism = synthetic construct
SEQUENCE: 23
agccctgcat tggtttgacc gcccaacctt                                     30

SEQ ID NO: 24         moltype = DNA  length = 30
FEATURE               Location/Qualifiers
source                1..30
                      mol_type = other DNA
                      note = sgRNA-2 targeted gene fragment
                      organism = synthetic construct
SEQUENCE: 24
ataagatcat ggtcagcata tcagacggct                                     30

SEQ ID NO: 25         moltype = DNA  length = 24
FEATURE               Location/Qualifiers
source                1..24
                      mol_type = other DNA
                      note = sequencing results of sgRNA-1 targeted gene fragment
                       in WT plant
                      organism = synthetic construct
SEQUENCE: 25
ccctgcattg gtttgaccgc ccaa                                           24
```

-continued

```
SEQ ID NO: 26          moltype = DNA  length = 24
FEATURE                Location/Qualifiers
source                 1..24
                       mol_type = other DNA
                       note = sequencing results of sgRNA-2 targeted gene fragment
                        in WT plant
                       organism = synthetic construct
SEQUENCE: 26
gatcatggtc agcatatcag acgg                                            24

SEQ ID NO: 27          moltype = DNA  length = 14
FEATURE                Location/Qualifiers
source                 1..14
                       mol_type = other DNA
                       note = sequencing results of sgRNA-1 targeted gene fragment
                        in KO_#1 plant
                       organism = synthetic construct
SEQUENCE: 27
ccctgcccgc ccaa                                                       14

SEQ ID NO: 28          moltype = DNA  length = 20
FEATURE                Location/Qualifiers
source                 1..20
                       mol_type = other DNA
                       note = sequencing results of sgRNA-2 targeted gene fragment
                        in KO_#1 plant
                       organism = synthetic construct
SEQUENCE: 28
gatcatggtc agcatgacgg                                                 20

SEQ ID NO: 29          moltype = DNA  length = 21
FEATURE                Location/Qualifiers
source                 1..21
                       mol_type = other DNA
                       note = sequencing results of sgRNA-1 targeted gene fragment
                        in KO_#2 plant
                       organism = synthetic construct
SEQUENCE: 29
ccctgcaggt ttgaccgccc a                                               21

SEQ ID NO: 30          moltype = DNA  length = 18
FEATURE                Location/Qualifiers
source                 1..18
                       mol_type = other DNA
                       note = sequencing results of sgRNA-2 targeted gene fragment
                        in KO_#2 plant
                       organism = synthetic construct
SEQUENCE: 30
gatcatggtc agcgacgg                                                   18
```